(12) United States Patent
Ho

(10) Patent No.: US 12,076,288 B2
(45) Date of Patent: Sep. 3, 2024

(54) INFLATABLE NECK TRACTION DEVICE

(71) Applicant: Hoi Ming Michael Ho, Tuen Mun (HK)

(72) Inventor: Hoi Ming Michael Ho, Tuen Mun (HK)

( * ) Notice: Subject to any disclaimer, the term of this patent is extended or adjusted under 35 U.S.C. 154(b) by 569 days.

(21) Appl. No.: 17/147,448

(22) Filed: Jan. 12, 2021

(65) Prior Publication Data
US 2022/0000698 A1    Jan. 6, 2022

(30) Foreign Application Priority Data

Jul. 3, 2020    (CN) .......................... 202010631822.5
Dec. 14, 2020   (CN) .......................... 202011467755.4

(51) Int. Cl.
*A61H 1/02*    (2006.01)

(52) U.S. Cl.
CPC ... *A61H 1/0222* (2013.01); *A61H 2201/0103* (2013.01); *A61H 2201/1609* (2013.01);
(Continued)

(58) Field of Classification Search
CPC .... A61H 2201/0103; A61H 2201/0207; A61H 2201/10; A61H 2201/1604–1616; A61H 2205/04; A61H 1/00; A61H 1/006; A61H 1/0218–0229; A61H 1/0296; A61H 39/002; A61H 39/06; A61H 2001/0233; A61H 2201/1609; A61H 2201/1614;
(Continued)

(56) References Cited

U.S. PATENT DOCUMENTS 3,343,532 A * 9/1967 Zumaglini ............. A61F 5/055
                                                            602/18
4,805,603 A    2/1989 Cumberland
(Continued)

FOREIGN PATENT DOCUMENTS

CN    101778612 A    7/2010
CN    106136748 A   11/2016
(Continued)

OTHER PUBLICATIONS

Kim, Kyu Ho; KR102044813B1 Pillow eith Air Cell; Nov. 15, 2019; p. 1-6; Translation downloaded from Espacenet on Jul. 6, 2023. (Year: 2023).*

*Primary Examiner* — Kendra D Carter
*Assistant Examiner* — Maap Ahmed Ellabib
(74) *Attorney, Agent, or Firm* — CIPO IP Group

(57) ABSTRACT

An inflatable neck traction device includes a supporting portion and a bearing portion. The height of the top surface of the bearing portion is lower than that of the supporting portion. The supporting portion has a neck support body and two shoulder abutting bodies, and can be provided therein with a first airbag and two second airbags. An inflation device can be connected to the airbags. When a user rests on the device in a supine position, the top surface of the neck support body supports the neck, and the shoulder abutting bodies abut against the shoulders. The inflation device inflates or deflates the airbags to displace the neck support body along a first axis and the shoulder abutting bodies along a second axis to change the force exerted by the neck support body and shoulder abutting bodies on the neck and shoulders to achieve cervical traction effects.

13 Claims, 30 Drawing Sheets

(52) U.S. Cl.
CPC .............. *A61H 2201/1614* (2013.01); *A61H 2203/0456* (2013.01); *A61H 2205/04* (2013.01); *A61H 2205/062* (2013.01)

(58) Field of Classification Search
CPC ............ A61H 2205/062; A61H 1/0222; A61H 9/0078; A61F 5/00; A61F 5/042; A61F 5/048; A61F 5/05816; A47G 9/0078; A47G 9/10; A47G 9/1027; A47G 9/1081; A61N 1/04; A61N 1/0456; A61N 1/36
See application file for complete search history.

(56) References Cited

U.S. PATENT DOCUMENTS

| | | | |
|---|---|---|---|
| 6,230,347 B1 | 5/2001 | Alexander | |
| 8,176,921 B2 | 5/2012 | Bazargani | |
| 8,684,958 B1 | 4/2014 | Lefkovitz | |
| 2009/0204046 A1 | 8/2009 | Chitwood et al. | |
| 2010/0121243 A1* | 5/2010 | Aune, Jr. | A61H 1/0296 602/32 |
| 2010/0198121 A1* | 8/2010 | Tago | A61H 9/0078 601/150 |
| 2014/0083434 A1* | 3/2014 | Groteke | A61N 1/0456 128/845 |
| 2015/0141894 A1* | 5/2015 | Graham | A61F 5/05816 602/36 |
| 2018/0318581 A1* | 11/2018 | Ho | A61H 39/04 |
| 2019/0110617 A1 | 4/2019 | Berney et al. | |
| 2021/0007926 A1* | 1/2021 | Wang | A61H 23/0263 |
| 2022/0054864 A1* | 2/2022 | Baldoni | A61N 2/002 |

FOREIGN PATENT DOCUMENTS

| | | | | |
|---|---|---|---|---|
| CN | 107149515 A | | 9/2017 | |
| CN | 208017633 U | | 10/2018 | |
| CN | 109568100 A | | 4/2019 | |
| CN | 208958444 U | | 6/2019 | |
| CN | 109998332 A | * | 7/2019 | ............ A47G 9/109 |
| CN | 209154138 U | | 7/2019 | |
| CN | 110604686 A | | 12/2019 | |
| CN | 210124886 U | | 3/2020 | |
| CN | 111053636 A | | 4/2020 | |
| CN | 210810302 U | | 6/2020 | |
| IN | 205832140 U | | 12/2016 | |
| JP | H18-2006325790 A | | 12/2006 | |
| KR | 20120064949 A | | 6/2012 | |
| KR | 102044813 B1 | * | 11/2019 | ............ A47G 9/1027 |
| KR | 20210113721 A | * | 9/2021 | ............ A47G 9/1027 |
| RU | 68290 U1 | | 11/2007 | |
| RU | 2444336 C1 | | 3/2012 | |
| RU | 2612842 C1 | | 3/2017 | |
| RU | 175498 U1 | | 12/2017 | |
| RU | 188899 U1 | | 4/2019 | |
| TW | I622388 B | | 5/2018 | |
| WO | 2018133466 A1 | | 7/2018 | |
| WO | 2018152676 A1 | | 8/2018 | |

* cited by examiner

INFLATABLE NECK TRACTION DEVICE

CROSS-REFERENCE TO RELATED PATENT APPLICATION

This non-provisional application claims priority to and the benefit of, under 35 U.S.C. § 119(a), Chinese Patent Application No. 202011467755.4, filed in the People's Republic of China on Dec. 14, 2020, and Chinese Patent Application No. 202010631822.5, filed in the People's Republic of China on Jul. 3, 2020. The entire content of the above identified applications are incorporated herein by reference.

FIELD

The present disclosure relates to a neck traction device, and more particularly to a neck traction device provided with three independent airbags therein, so that a user can inflate or deflate the airbags by himself or herself, thereby changing the appearance, size and firmness of the neck traction device, and adjusting the force exerted by the neck traction device on the neck and/or shoulder(s) of the user, so as to achieve the effects of neck traction. The neck traction device of the present disclosure is easy to use by a user needing traction without help from others, resembles a comfortable pillow, and the user can use while he or she is laying down or is sleeping.

BACKGROUND

Cervical vertebrae connect the skull on the superior side and the thoracic spine on the inferior side, and their importance is self-evident. However, people in modern time are suffering from cervical spondylosis (also referred to as cervical spine syndromes) more because of inappropriate life style habits (such as prolonged use of mobile phones, game consoles or computers with the head lowered down, or improper standing or sitting posture), work needs (such as driving) that keep the neck at a fixed posture for a long time, or excessive psychological pressure, etc. These factors cause a user's neck muscles to become increasingly tense over time, and even lead to cervical spine joint degeneration, or intervertebral discs degeneration and herniation (as they undertake excessive compression), leading to greater proneness to nerve impingement, arthritis, joint pain, and premature degeneration or thinning of intervertebral discs, etc., and eventually the development of symptoms such as throbbing arm pain, arm numbness, chronic headache, chronic neck and shoulder pain, etc.

Most cervical spondylosis, especially chronic neck and shoulder dysfunction, can be caused by conditions such as tightness of the neck and upper shoulder muscles or excessive compression of the cervical spine joints and intervertebral discs that cause nerve irritation and impingements. Such a patient can suffer from neck and shoulder pain almost every day, and the pain can become worse especially after a whole day of work, making it difficult for the patient to relax and fall asleep at night. In addition, an ordinary pillow available on the market provide little, if not none, benefit to a patient with cervical spondylosis; rather, after resting on such a pillow for a long time, the patient can suffer from more severe neck and shoulder pain, headache and/or arm pain or numbness. In general, for patients with chronic neck and shoulder dysfunction, doctors may recommend cervical traction therapy to help reduce pressure between multiple intervertebral discs and relax the neck and shoulder muscles, and to reduce pressure and irritation on paraspinal nerves, thereby alleviating neck and shoulder pain. The act of separating the joint(s) and stretching connecting muscles loose with an external force is called "traction". Traction not only has an effect on the joints, but also relaxes tight muscles, tendons and/or ligaments, and reduces pressure and irritation on paraspinal nerves, and therefore can alleviate pain, numbness and improve joint mobility.

However, in reality, most patients often cannot afford the time or money required for the conventional treatment, resulting in such patients not receiving treatment and suffering pain that could have been alleviated. In addition, cervical traction includes manual traction and mechanical traction, and these two methods must be performed by rigorously trained medical professionals. Nevertheless, many of the patients receiving conventional treatments have not been attended by proper medical professional capable of providing appropriate treatment the patients need. Therefore, such patients' pain has not been effectively relieved. In the case of having received no treatment or ineffective treatment, some patients try to take painkillers, use ointments or patches, etc. However, their effects are limited, and long-term use of such can have serious side effects.

Further, traditional neck traction devices also suffer from the following issues. Traditionally, traction to the cervical spine is usually done with a head/neck harness that pulls the head longitudinally away from the neck. These devices used in physiotherapy clinics utilize counter weights or are powered by electrical motors. These traditional neck traction devices are not easy to use, often require the help of medical professionals, and are cumbersome and uncomfortable. Traditional neck traction devices cannot be used as a sleeping pillow while a user is laying down or sleeping.

That is, many people have suffered from chronic headaches, neck and shoulder dysfunction and the resulting pain due to neck muscles tightness, excessive compression of cervical spine joints, herniated intervertebral discs, impingement plus irritation of paraspinal nerves, etc., and therefore from deteriorated health condition and life quality, without a good solution being availed. Accordingly, effectively solving the aforementioned issue, so that people do not need to spend huge amount of time and/or money on cervical traction, but can independently bear out cervical traction, has become an important subject of the present disclosure.

SUMMARY

In one aspect, the present disclosure is directed to a neck traction device including from the front to the rear a supporting portion and a bearing portion. The supporting portion includes a neck support body, two shoulder abutting bodies, a first airbag, two second airbags, and an inflation device. The bearing portion can bear an occiput of a user when the user is in a supine position. A height of a top surface of the bearing portion is lower than a height of a top surface of the supporting portion. The neck support body is located at a center portion of the supporting portion. The neck support body has a top surface configured to support the neck of a user, and a bottom surface concavely provided with a first groove. The two shoulder abutting bodies respectively extends from a front side of the supporting portion. The two shoulder abutting bodies have front surfaces configured to abut against shoulders of the user. One of the shoulder abutting bodies is located at a position of the supporting portion that is nearer to a right side of the supporting portion than to a left side of the supporting portion. The other one of the shoulder abutting bodies is located at a position nearer to the left side of the supporting portion than to the right side of the supporting portion. A bottom surface of each of the shoulder abutting bodies is concavely provided with a second groove. The first airbag can be accommodated within the first groove, expand or contract along a first axis, and displace a top surface of the neck support body along the first axis. Each of the two second airbags can be accommodated within a corresponding one of the second grooves, expand or contract along a second axis perpendicular or substantially perpendicular to the first axis, and displace a front surface of a corresponding one of the shoulder abutting bodies along the second axis. The inflation device can be connected to the first airbag and the second airbags, respectively, and inflate or deflate the first airbag and the second airbags together, or separately, to change expansion or contraction degrees of the first airbag and the second airbags. Furthermore, the inflation device can be either a manually operated, or a powered inflation device. Therefore, a user can operate the inflation device to adjust the expansion or contraction degrees of the first airbag and the second airbags by himself or herself, so as to change the force exerted by the neck support body and shoulder abutting bodies on the neck and shoulders of the user to achieve cervical traction effects.

In certain embodiments, the neck traction device is further concavely provided with two third grooves located at opposite sides of the first groove, and further includes two third airbags, each can be accommodated within a corresponding one of the third grooves, expand or contract along the first axis, and displace a top surface of the neck traction device along the first axis.

In certain embodiments, the inflation device includes a plurality of pipe bodies, a first air valve that can be assembled to one of the pipe bodies, at least one second air valve that can be assembled to another one of the pipe bodies, and at least one inflation portion. The inflation portion can be connected to the first airbag and the second airbags through the pipe bodies, inflate or deflate the first airbag when the first air valve is opened, and inflate or deflate the second airbags when the second air valve is opened.

In certain embodiments, the first airbag can expand to a maximum expansion state with a maximum length of the first airbag in a direction of a first axis being 75 mm to 85 mm.

In certain embodiments, each of the second airbags can expand to a maximum expansion state with a maximum length of the second airbag in a direction of a second axis being 55 mm to 65 mm.

In certain embodiments, the neck traction device further includes a plurality of physical therapy portions, each corresponding to a position of the neck support body and can abut against the neck of the user and be electrically connected to a physical therapy device to receive electric power transmitted from the physical therapy device.

In certain embodiments, at least one of the physical therapy portions is arranged with an electrotherapy unit that can receive the electric power transmitted from the physical therapy device and output electrical stimulation to the neck of the user.

In certain embodiments, at least one of the physical therapy portions is arranged with a heat therapy unit that can receive the electric power transmitted from the physical therapy device and generate heat to heat the neck of the user.

In certain embodiments, at least one of the physical therapy portions is arranged with a combined electrotherapy-heat therapy unit that can receive the electric power transmitted from the physical therapy device, output electrical stimulation to the neck of the user and generate heat to heat the neck.

In certain embodiments, the neck traction device includes a pillow body and a pillowcase that can cover the pillow body. The neck support body and the shoulder abutting bodies are arranged on the pillow body, the first airbag and the second airbags are arranged within the pillow body, the physical therapy portions are provided on the pillowcase, the inflation device is external to the pillow body and the pillowcase, and the pipe bodies can extend into the pillow body through the pillowcase.

This and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION

Figure 1:
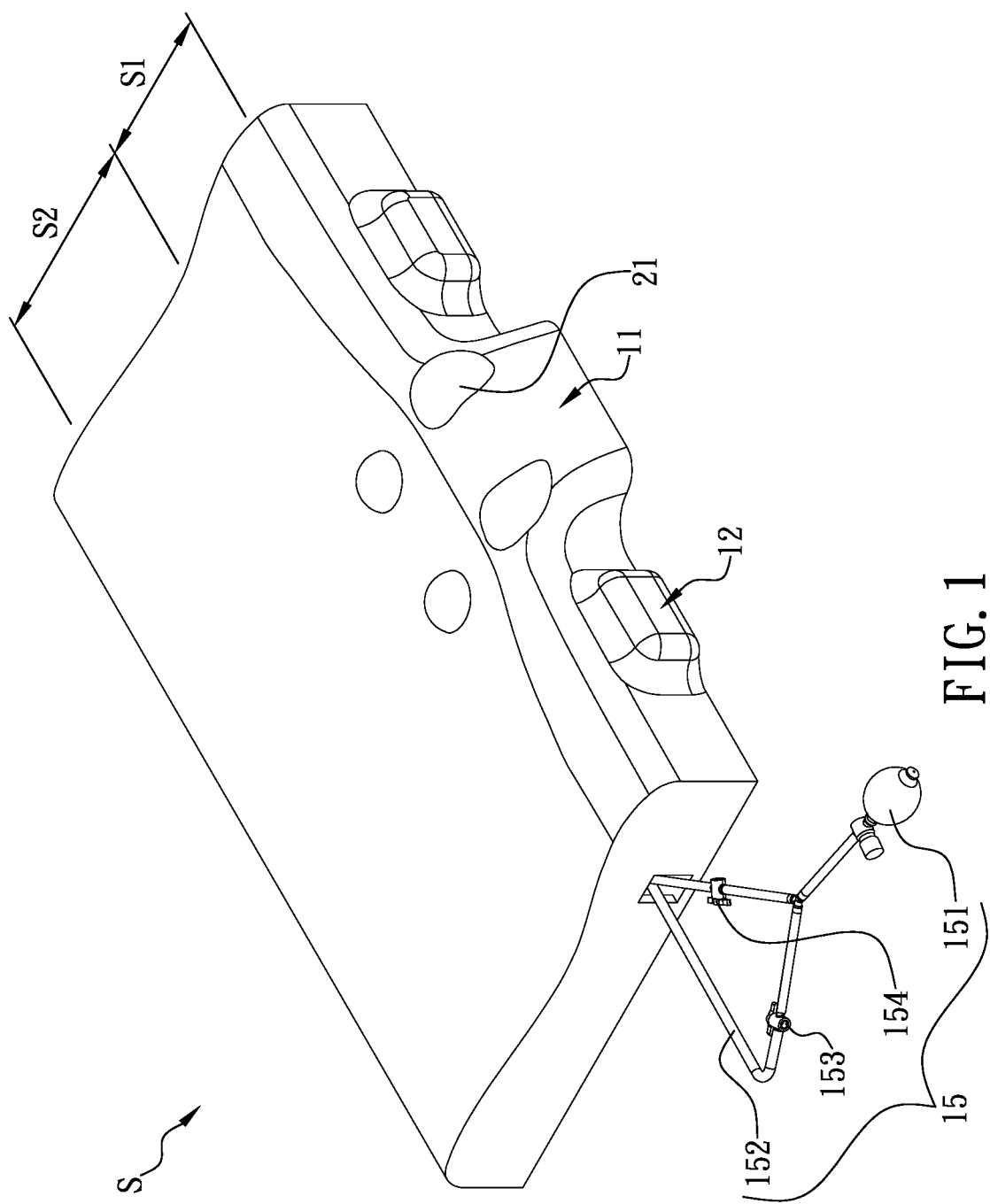
FIG. 1 is a schematic view of the neck traction device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, parts or the like, which are for distinguishing one component/part from another one only, and are not intended to, nor should be construed to impose any substantive limitations on the components, parts or the like, or be relevant to the sequence in which the components/parts are to be assembled or disposed in practical application.

As used herein, the term "substantially" or "approximately" refers to, for example, a value, or an average of values, in an acceptable deviation range of a particular value recognized or decided by a person of ordinary skill in the art, taking into account any specific quantity of errors related to the measurement of the value that may resulted from limitations of a measurement system or device. For example, "substantially" may indicate that the value is within, for example, ±5%, ±3%, ±1%, ±0.5% or ±0.1%, or one or more standard deviations, of the particular value.

One aspect of the present disclosure is directed to an inflatable neck traction device. To facilitate understanding only, unless the context clearly dictates otherwise, the lower right side of FIG. 1 is designated as the front sides of the components shown in FIG. 1, the upper left side of FIG. 1 is designated as the rear sides of the components, the upper right side of FIG. 1 is designated as the right sides of the components, the lower left side of FIG. 1 is designated as the left sides of the components, the top side of FIG. 1 is designated as the top sides of the components, and the bottom side of FIG. 1 is designated as the bottom sides of the components. However, the present disclosure is not limited thereto. In certain embodiments, a neck traction device S can be divided from the front to the rear at least into a supporting portion S1 and a bearing portion S2. The shape of the top surfaces of the supporting portion S1 and the bearing portion S2 is ergonomically designed to fit the natural curvature of the cervical spine, so that the height of the top surface of the bearing portion S2 is lower than the height of the top surface of the supporting portion S1.

Figure 2:
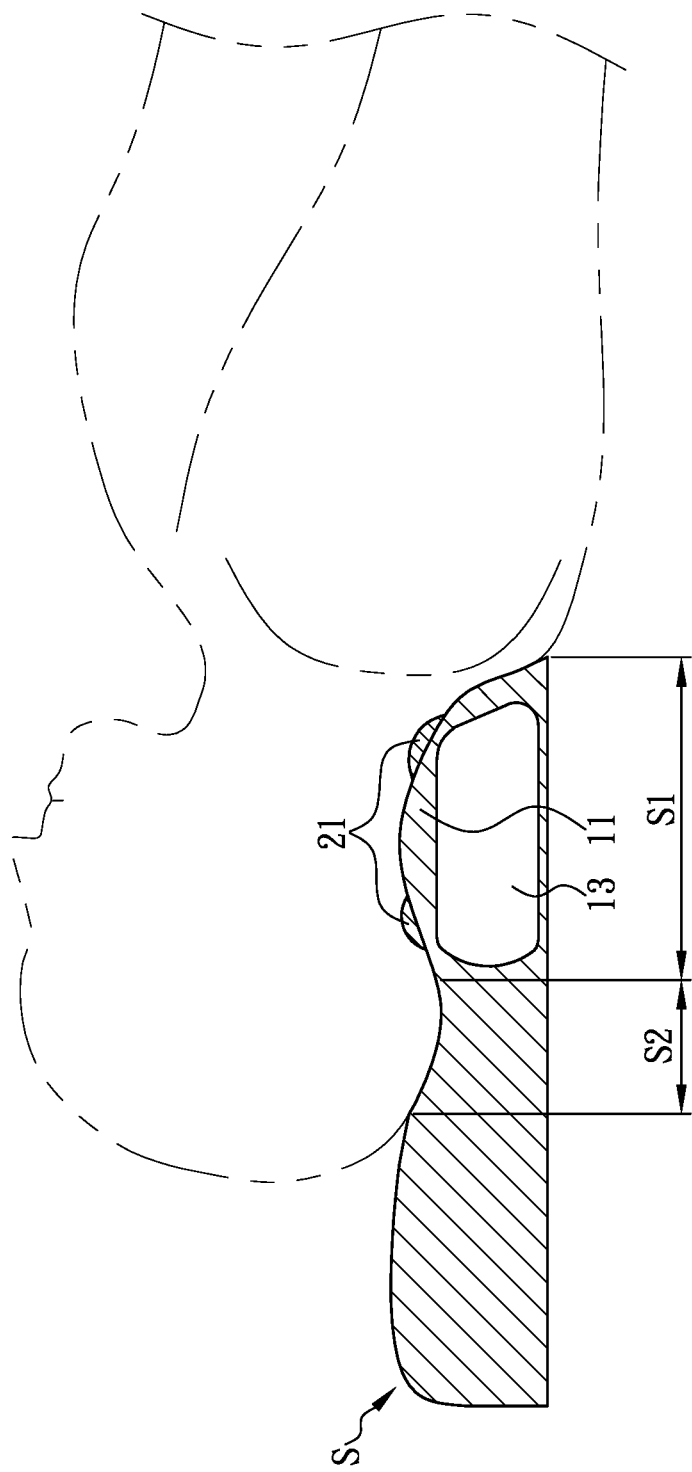
FIG. 2 is a side view showing a user resting on the neck traction device according to the present disclosure.

Referring to FIGS. 1 and 2, when a user rests on the neck traction device S in a supine position, the bearing portion S2 corresponds to and bears the occiput of the user (as shown in FIG. 2), while the supporting portion S1 corresponds to and supports the neck of the user. The contour of the supporting portion S1 matches the natural cervical lordosis of the human cervical spine to provide corresponding support force, so as to help the user to restore the alignment and posture of his or her cervical spine to the natural states. In addition, because the neck traction device S has elasticity, when a user rests on the neck traction device S, the neck traction device S deforms so that the top surface fits the contour of the head and neck of the user, and achieves the bearing and supporting effects.

Figure 3:
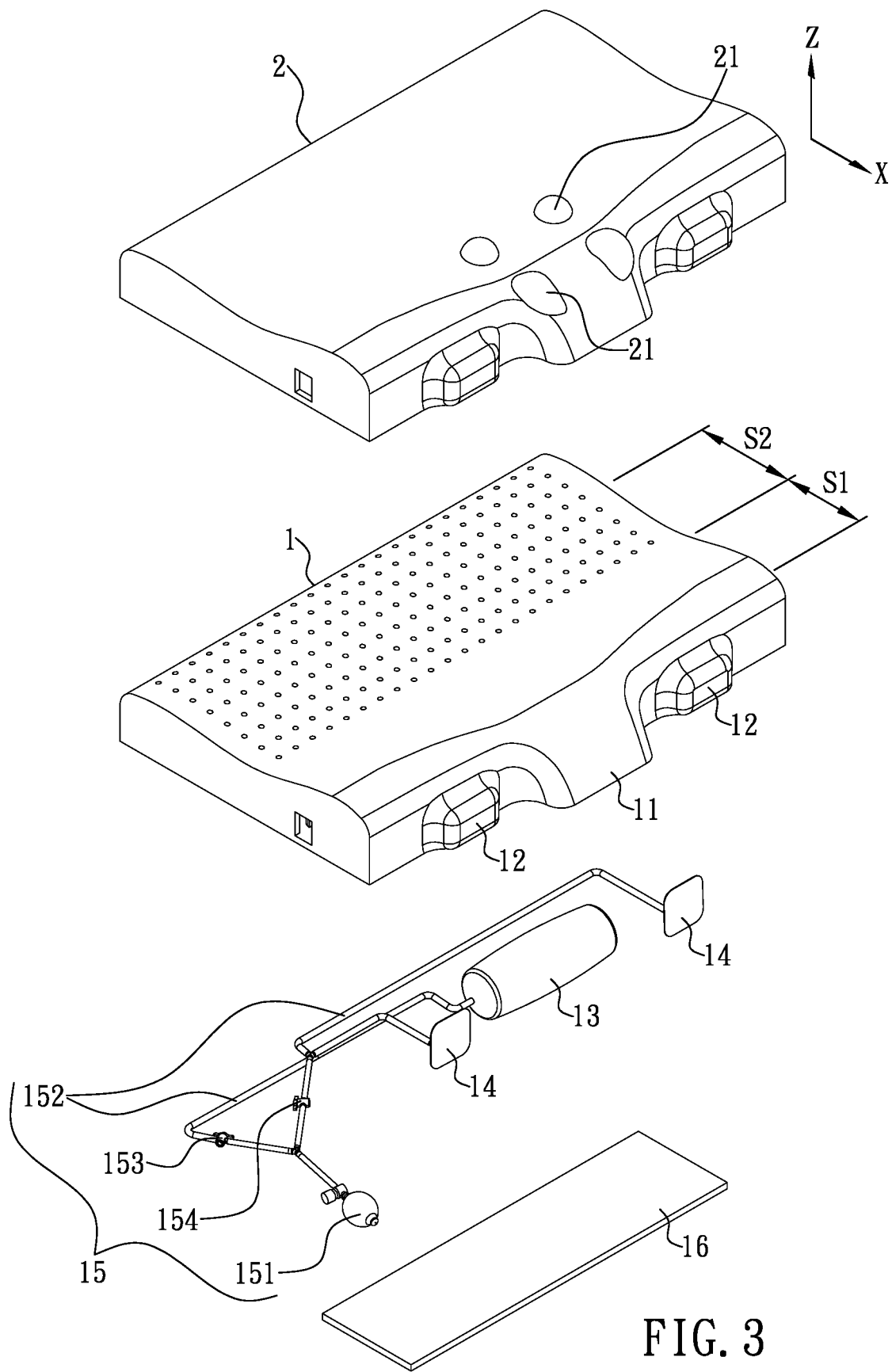
FIG. 3 is a top exploded view of the neck traction device according to the present disclosure.
Figure 4:
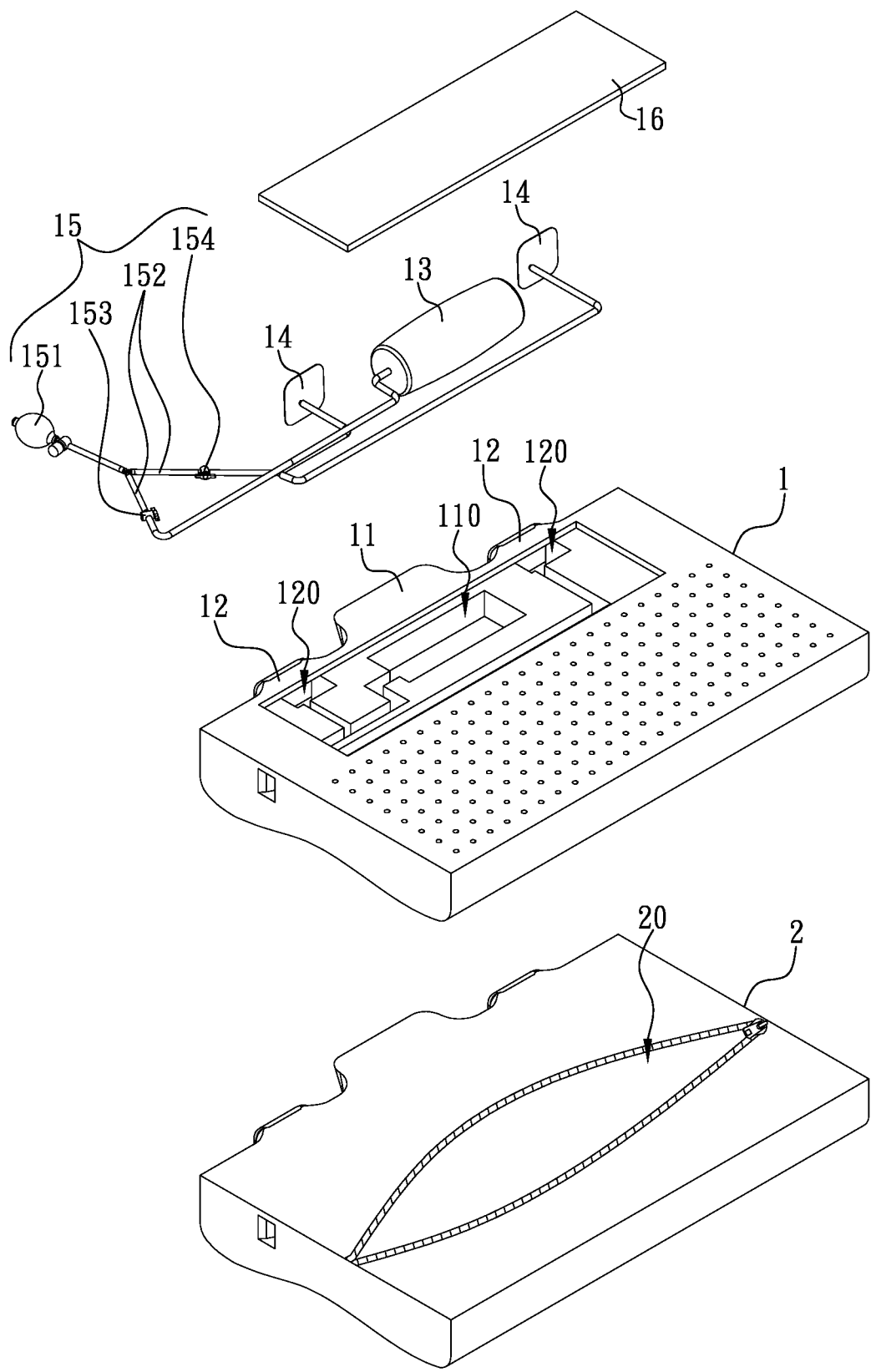
FIG. 4 is a bottom exploded view of the neck traction device according to the present disclosure.

Referring to FIGS. 3 and 4, the neck traction device S includes a pillow body 1 and a pillowcase 2. The pillowcase 2 is provided with an accommodating space 20 and is configured to cover the pillow body 1, so that the pillow body 1 can be positioned in the accommodating space 20. As the contour of the pillow case 2 matches that of the pillow body 1, when the pillow body 1 is placed in the pillow case 2, the structure of the pillow body 1 can still be clearly indicated through the contour of the pillow case. Accordingly, in FIG. 1, for ease of description only, the positions of the components of the pillow body 1 to be described infra are also indicated on the corresponding positions on pillowcase 2.

Referring again to FIGS. 3 and 4, in certain embodiments, the pillow body 1 can be made of foamed material and/or other elastomer, and/or filling/packing material, and have the supporting portion S1 and the bearing portion S2. The center portion of the supporting portion S1 is provided with a neck support body 11. The top surface of the neck support body 11 can support the neck of the user (as shown in FIG. 2). In addition, in order to better achieve the effect of neck supporting, the front side of the neck support body 11 extends forward, so as to completely or nearly completely support the user's neck. Accordingly, when the neck support body 11 abuts and supports the user's neck, the head of the user will naturally tilt backward, which helps to fix more stably the head of the user to the bearing portion S2.

Figure 5:
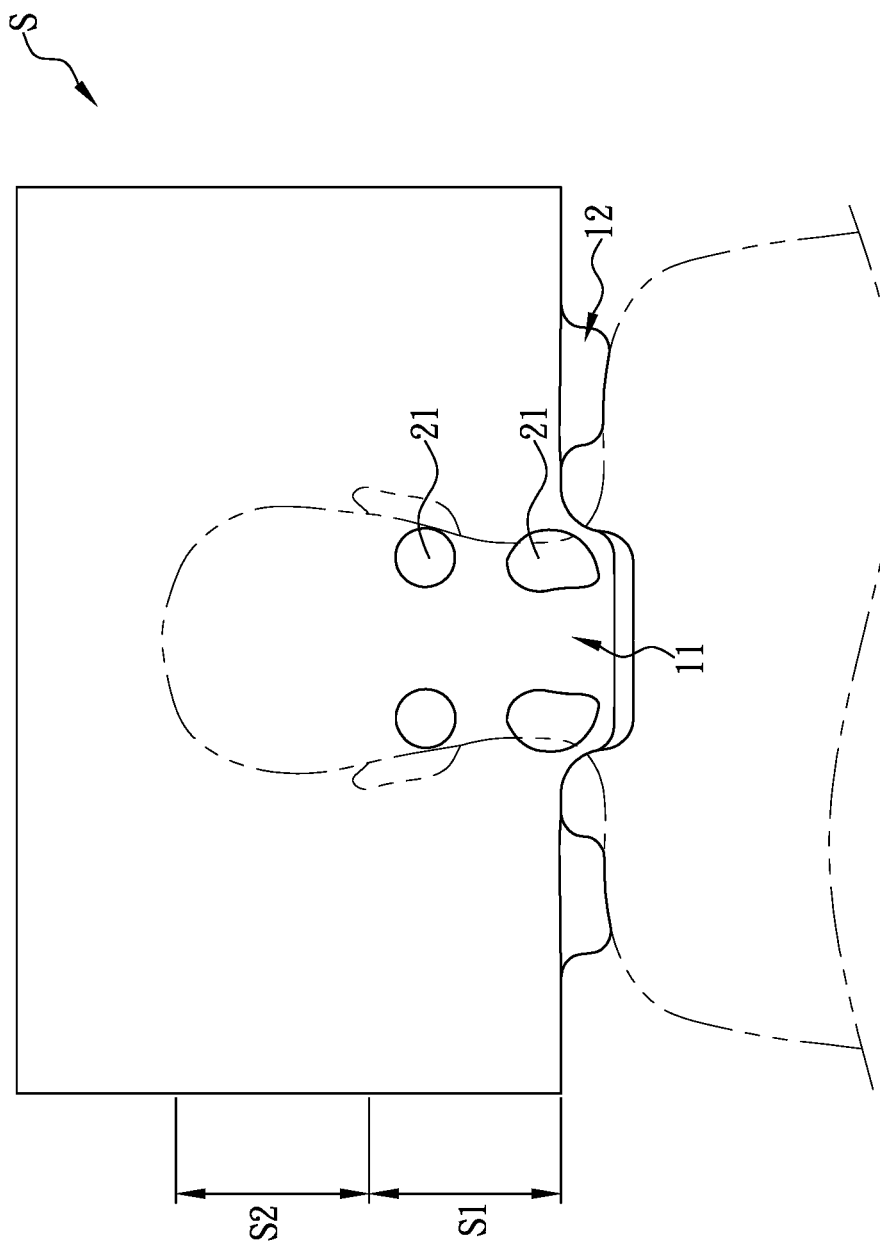
FIG. 5 is a top view of a user resting on the neck traction device according to the present disclosure.

Referring again to FIGS. 3 and 4, the supporting portion S1 is further provided with two shoulder abutting bodies 12. The two shoulder abutting bodies 12 can be arranged on the two sides of the neck supporting body 11. In certain embodiments, one of the shoulder abutting bodies 12 can be located at a position on the supporting portion S1 that is nearer to the left side of the supporting portion S1 than to the right side thereof, and the other shoulder abutting body 12 can be located at a position on the supporting portion S1 that is nearer to the right side of the supporting portion S1 than to the left side thereof. The two shoulder abutting bodies 12 can extend from the front side of the supporting portion S1 respectively, and when the head of the user rests on the neck traction device S, the front sides of the two shoulder abutting bodies 12 can correspond to and be abutted against the shoulders of the user (as shown in FIG. 5).

As shown in FIGS. 3 and 4, the bottom surface of the neck support body 11 can be concavely provided with a first groove 110, and a first airbag 13 can be accommodated in the first groove 110. The first airbag 13 can be inflated to expand, or deflated to contract, along a first axis (for example, the Z axis shown in FIG. 3). When the first airbag 13 expands or contracts along the first axis, the expansion or contraction displaces the top surface of the neck support body 11 along the first axis, for example, upward or downward. In certain embodiments, when the first airbag 13 is inflated to expand to a first maximum expansion state, the maximum length of the first airbag 13 in the direction of the first axis is 75 mm to 85 mm. However, the present disclosure is not limited thereto. In addition, it is noted that as long as the first groove 110 can accommodate the first airbag 13, and allow the first airbag 13 to expand or contract to displace the top surface of the neck support body 11, the first groove 110 is defined as being located within the bottom surface of the neck support body 11.

Referring again to FIGS. 3 and 4, the bottom surface of each of the shoulder abutting bodies 12 can be concavely provided with a second groove 120, and two second airbags 14 can be accommodated in the second grooves 120, respectively. Each of the second airbags 14 can be inflated to expand, or deflated to contract, along a second axis (for example, the X axis shown in FIG. 3) that is perpendicular or substantially perpendicular to the first axis. When a second airbag 14 expands or contracts along the second axis, the expansion or contraction displaces the front surface of a corresponding shoulder abutting body 12 along the second axis, for example, forward or backward. In certain embodiments, when the second airbag 14 is inflated to expand to a second maximum expansion state, the maximum length of the second airbag 14 in the direction of the second axis is 55 mm to 65 mm. However, the present disclosure is not limited thereto. In addition, it is noted that as long as a second groove 120 can accommodate a second airbag 14, and allow the second airbag 14 to expand or contract to displace the front surface of the shoulder abutting body 12, the second groove 120 is defined as being located within the bottom surface of the shoulder abutting body 12.

Referring again to FIGS. 3 and 4, an inflation device 15 can be connected respectively to the first airbag 13 and second airbags 14 which are independent from each other. When the inflation device 15 is in operation, it can inflate or deflate the first airbag 13 and the two second airbags 14, and change the degrees of the expansion or contraction of the first airbag 13 and the two second airbags 14. In certain embodiments, the inflation device 15 includes an inflation portion 151, a plurality of pipe bodies 152, a first air valve 153, and a second air valve 154. The inflation portion 151 can be a hand press inflation pump. However, the present disclosure is not limited thereto, and in certain other embodiments the inflation portion 151 may be an electric inflation pump. The pipe bodies 152 can pass through the pillowcase 2 and the pillow body 1 to communicate with the first airbag 13 and the two second airbags 14, respectively, so that the inflation portion 151 can inflate or deflate the first and/or second airbags 13, 14 through the pipe bodies 152. The first air valve 153 can be assembled to one of the pipe bodies 152, and the pipe body 152 can communicate with the first air bag 13, while the second air valve 154 can be assembled to another pipe body 152 that is to communicate with the second airbags 14.

As shown in FIGS. 3 and 4, when the first air valve 153 is opened, the inflation portion 151 can inflate or deflate the first air bag 13. When the first air valve 153 is closed, the inflation portion 151 would not be able to inflate or deflate the first airbag 13. Similarly, when the second air valve 154 is opened, the inflation portion 151 can inflate or deflate the two second airbags 14 at the same time. When the second air valve 154 is closed, the inflation portion 151 would not be able to inflate or deflate the two second air bags 14.

While FIGS. 3 and 4 show only a single second air valve 154 to simultaneously adjust the degrees of inflation or deflation of the two second airbags 14, in certain embodiments, two second air valves 154 can be provided to independently adjust the degrees of inflation or deflation of any of the second airbags 14. In addition, in actual use, a user can open both the first air valve 153 and the second air valve 154, so that the inflation portion 151 can inflate the first airbag 13 and the second airbags 14 at the same time. A user can also open the first air valve 153 and close the second air valve 154, so as to improve the inflation efficiency of the first airbag 13. Similarly, a user can open the second air valve 154 and close the first air valve 153, so as to improve the inflation efficiency of the second airbags 14.

Figure 6:
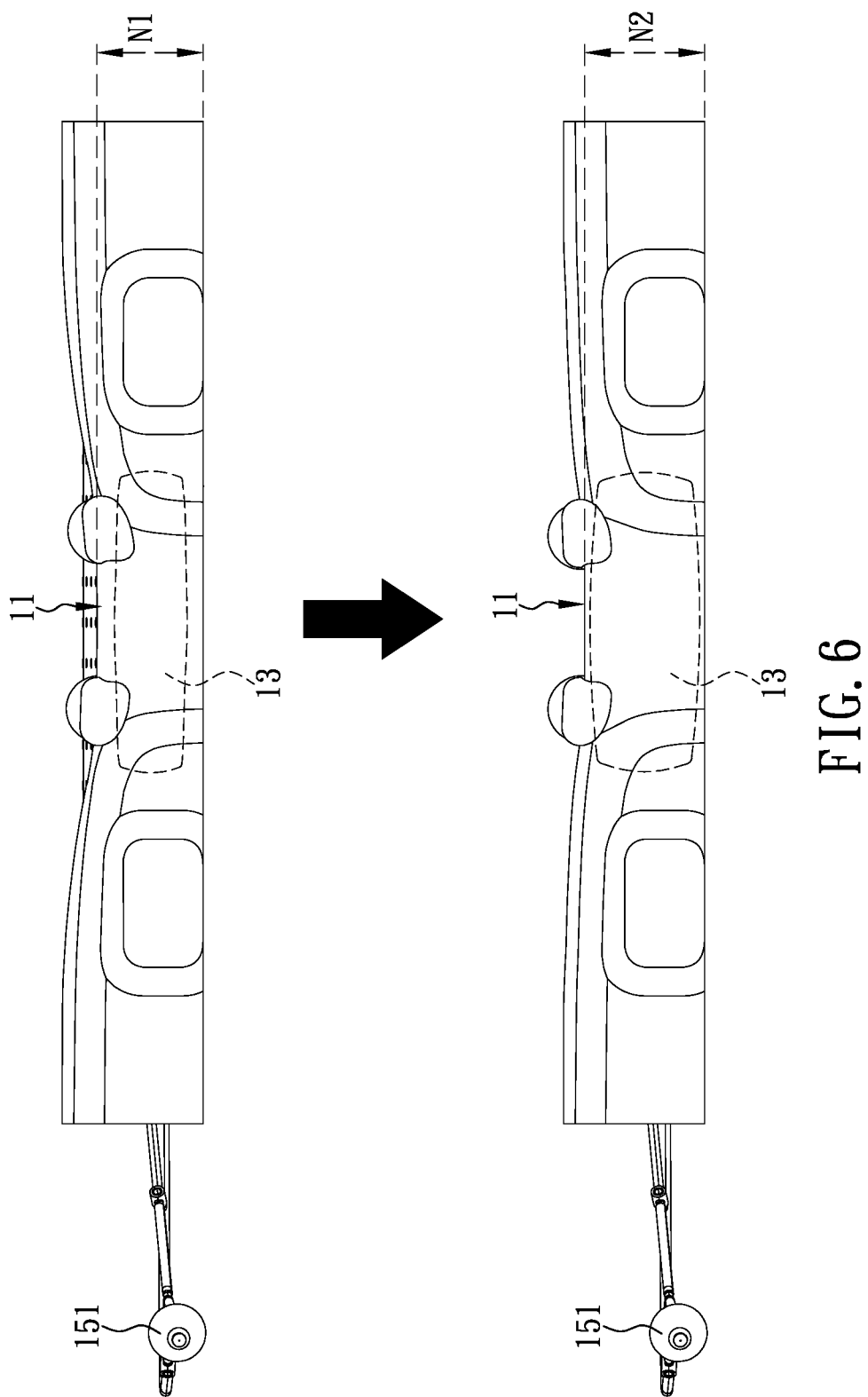
FIG. 6 is a schematic diagram showing the inflation change of a first airbag of the neck traction device according to the present disclosure.

Referring to FIGS. 1, 2 and 6, when the head of a user rests on the neck traction device S, the first air bag 13 can be inflated through the inflation portion 151. At this time, the first air bag 13 gradually expands, so that the top surface of the neck support body 11 is gradually moved upward, thereby pushing the user's neck upward, and the user's cervical spine can return to its natural lordotic curvature, and present an arch shape. The height of the top surface, or more precisely a point of the top surface that corresponds to the highest point of the first airbag 13 along the z axis shown in FIG. 3, of the neck support body 11 relative to the bottom surface of the neck support body 11 when the top surface is not displaced by the expansion of the first air bag 13 can be defined as a first height N1. The height of the top surface, or more precisely a point of the top surface that corresponds to the highest point of the first airbag 13 along the z axis shown in FIG. 3, of the neck support body 11 relative to the bottom surface of the neck support body 11 when the top surface is displaced by the first air bag 13 expanding to the first maximum expansion state can be defined as a second height N2. In certain embodiments, the ratio of the first height N1 to the second height N2 can range between 1:1.10 and 1:1.70, and in certain embodiments, between 1:1.26 and 1:1.46. Accordingly, by the design of the first airbag 13, the height and the firmness of an area of the neck traction device S that abuts against and corresponds to the neck of a user when the user is lying on the neck traction device S can be adjusted to keep the neck of the user at a proper position and allow the cervical vertebrae of the user to be aligned properly.

Figure 7:
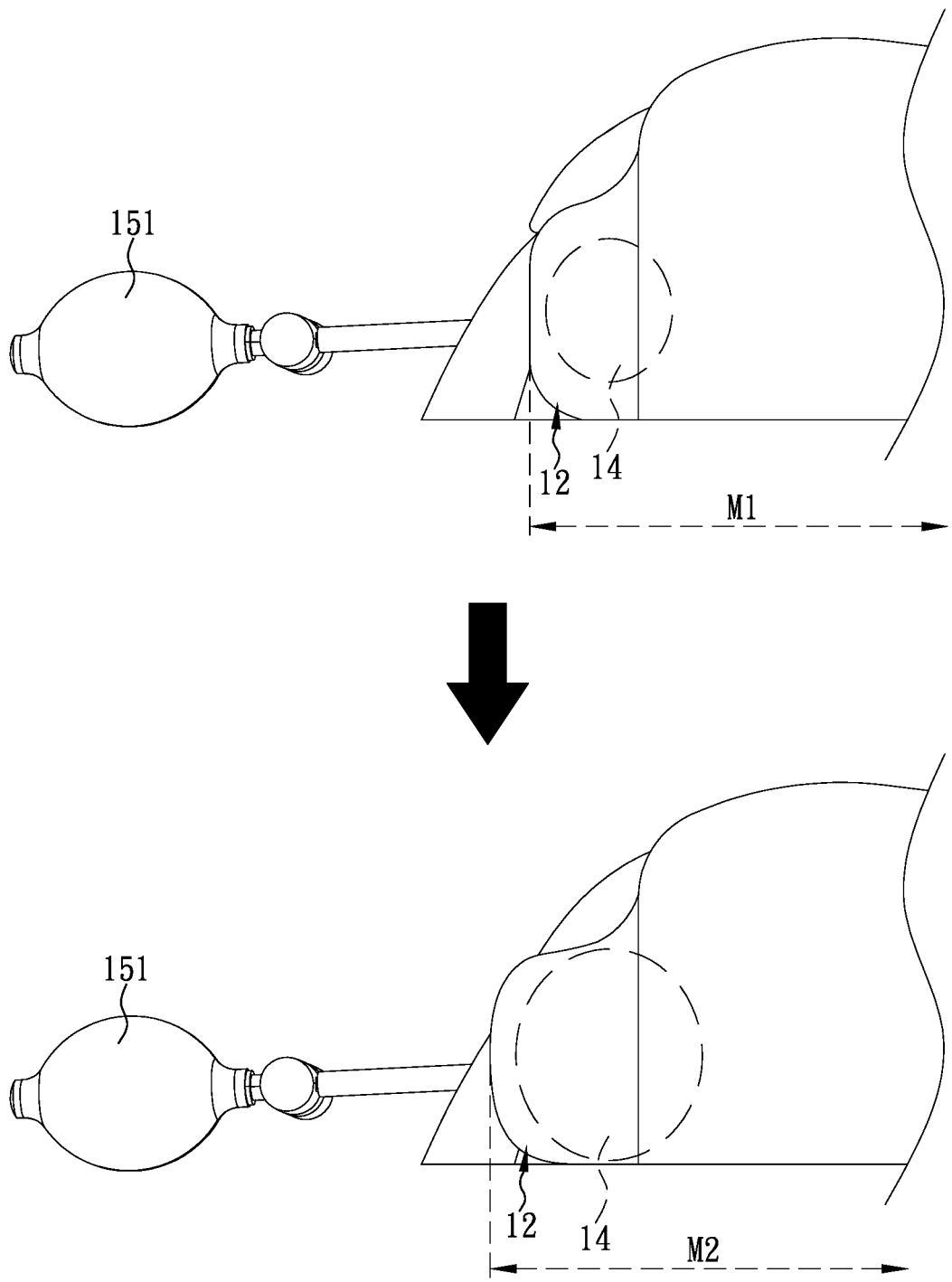
FIG. 7 is a schematic diagram showing the inflation change of a second airbag of the neck traction device according to the present disclosure.

Also, as shown in FIGS. 5 and 7, when the inflation portion 151 inflates the two second airbags 14, the two second airbags 14 gradually expand so that the front surfaces of the two shoulder abutting bodies 12 gradually move forward, thereby pushing the shoulder(s) of the user forward (i.e., in the direction to the foot of the user). Referring to FIG. 7, a length from the front surface of the shoulder abutting body 12 to the rear surface of the pillow body 1 when the front surface of the shoulder abutting body 12 is not displaced by the expansion of a corresponding second air bag 14 can be defined as a first length M1. A length from the front surface of the shoulder abutting body 12 to the rear surface of the pillow body 1 when the front surface of the shoulder abutting body 12 is displaced by a corresponding second air bag 14 expanding to the second maximum expansion state can be defined as a second length M2. In certain embodiments, the ratio of the first length M1 to the second length M2 can range between 1:1.01 and 1:1.15, and in certain embodiments, between 1:1.04 and 1:1.12.

Figure 8:
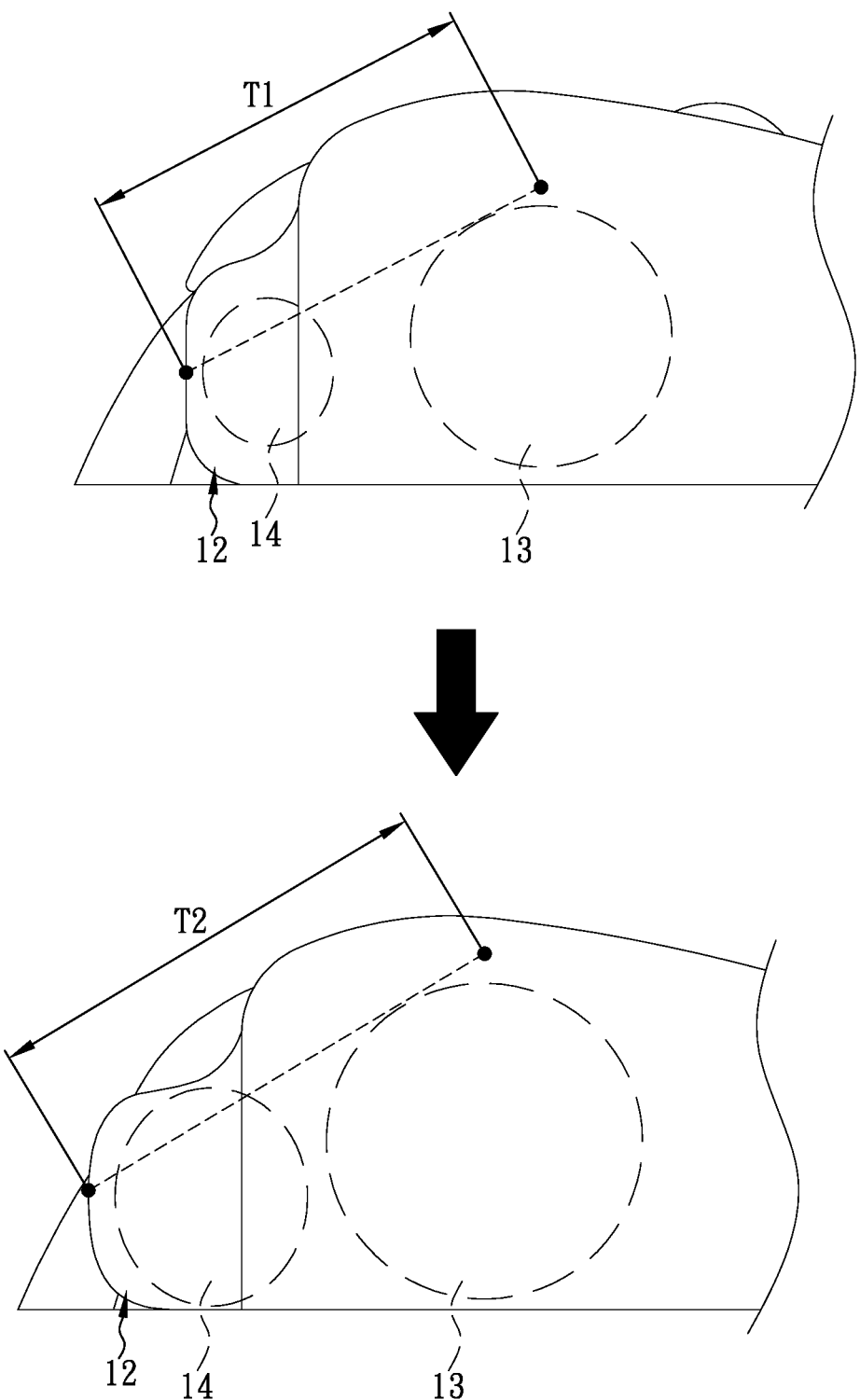
FIG. 8 is a schematic diagram showing the inflation change of the first and second airbags of the neck traction device according to the present disclosure.

Further, referring to FIG. 8, as the top surface of the neck support body 11 is moved along the first axis, for example, upward, when the first air bag 13 expands, and the front surface of a shoulder abutting body 12 is moved along the second axis, for example, forward, when the corresponding second airbag 14 expands, when observed laterally, the head and neck of a user rested on the neck traction device S would be located substantially along the hypotenuse as defined by the two moving directions, that is, the first and second axes, for example, upward and forward directions. Referring to FIGS. 3 and 8, a distance between the projection, on a plane defined by the first and second axes, for example, the x axis and z axis shown in FIG. 3, of a point of the top surface of the neck support body 11 that corresponds to the highest point of the first airbag 13 along the z axis and the projection of the center of a front surface of a shoulder abutting body 12 on the plane when the top surface of the neck support body 11 and the front surface of the shoulder abutting body 12 are not displaced by the expansion of the first air bag 13 and the corresponding second airbag 14 can be defined as a first distance T1. A distance between the projection on the plane that is of the point of the top surface of the neck support body 11 that corresponds to the highest point of the first airbag 13 and the projection on the plane that is of the center of the front surface of the shoulder abutting body 12 when the top surface of the neck support body 11 and the front surface of the shoulder abutting body 12 are displaced by the first air bag 13 and the corresponding second airbag 14 that are respectively in the first maximum expansion state and the second maximum expansion state can be defined as a second distance T2. In certain embodiments, the ratio of the first distance T1 to the second distance T2 can range between 1:1.30 and 1:1.95, and in certain embodiments, between 1:1.55 and 1:1.75.

In a situation where the head and the neck of the user are rested on the neck traction device S, since the head of the user is sunk into the bearing portion S2 and the neck is supported by the neck support body 11, the head and neck can act as an anchor and be positioned on the neck traction device S. When the two second airbags 14 are inflated, they push the shoulders of the user, respectively, away from the head, and generate a pulling force on the user's neck and shoulder muscles, thereby increasing the spaces between the intervertebral discs of the plural vertebrae of the cervical spine, which reduces the pressure in the intervertebral discs, and increasing the diameters of the neural foramina, which alleviates nerve compression syndromes. This mechanism works to stretch the neck and upper shoulder muscles of a user and to provide traction therapy to the cervical spine to relieve tight muscles and to decompress spinal disks in the cervical spine, and therefore reduces or removes pressure on spinal nerves that causes neck pain, upper shoulder pain and radiating numbness or pain in the upper extremities. In this way, by operating the inflation device 15, a user can adjust by himself or herself the inflation or deflation degrees of the first airbag 13 and the second airbags 14, thereby changing the force exerted on the neck and/or shoulder(s) of the user by the neck support body 11 and the shoulder abutting bodies 12, to achieve the effect of cervical traction by himself or herself.

Figure 9:
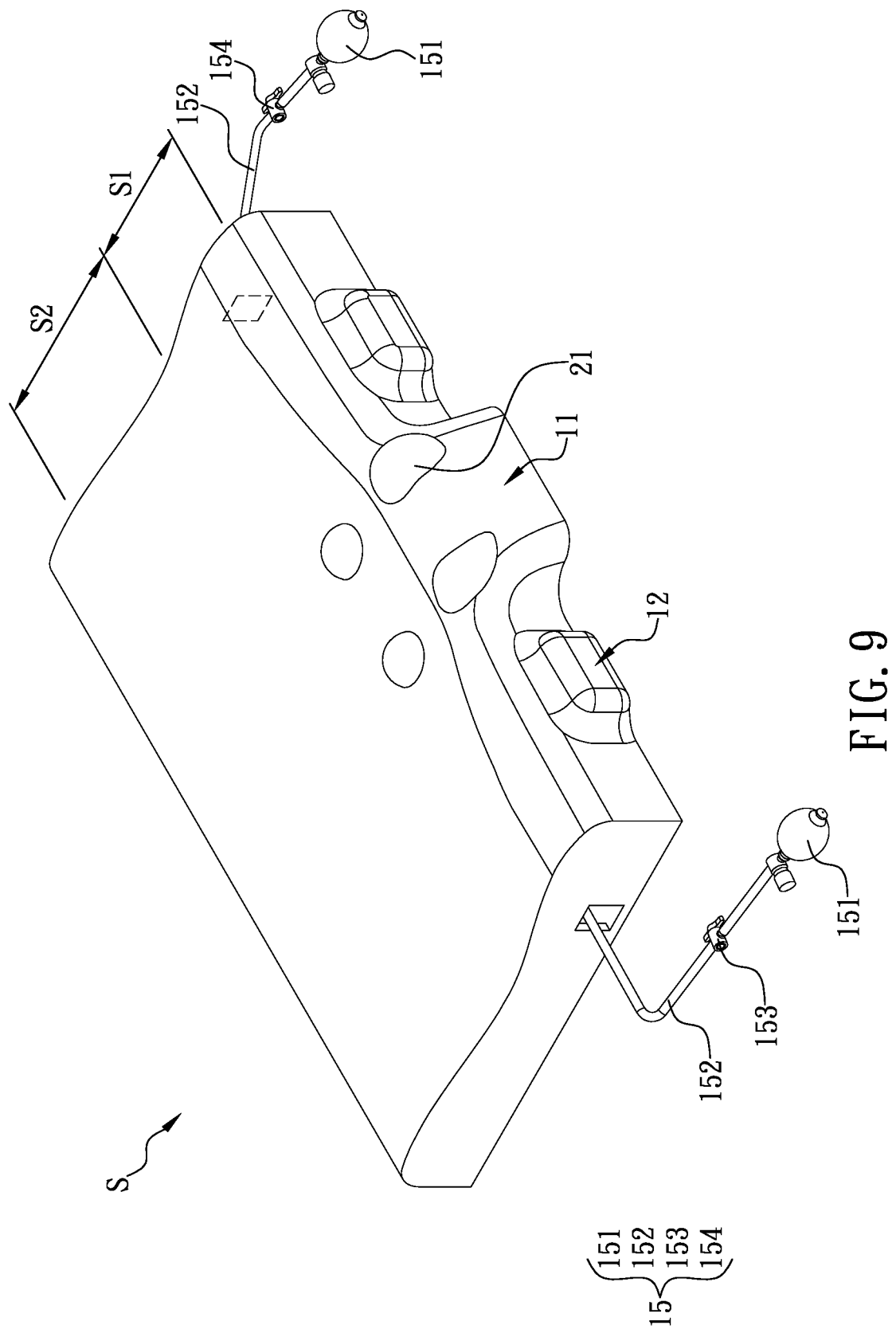
FIG. 9 is a schematic view of a neck traction device having a plurality of inflation portions according to the present disclosure.
Figure 10:
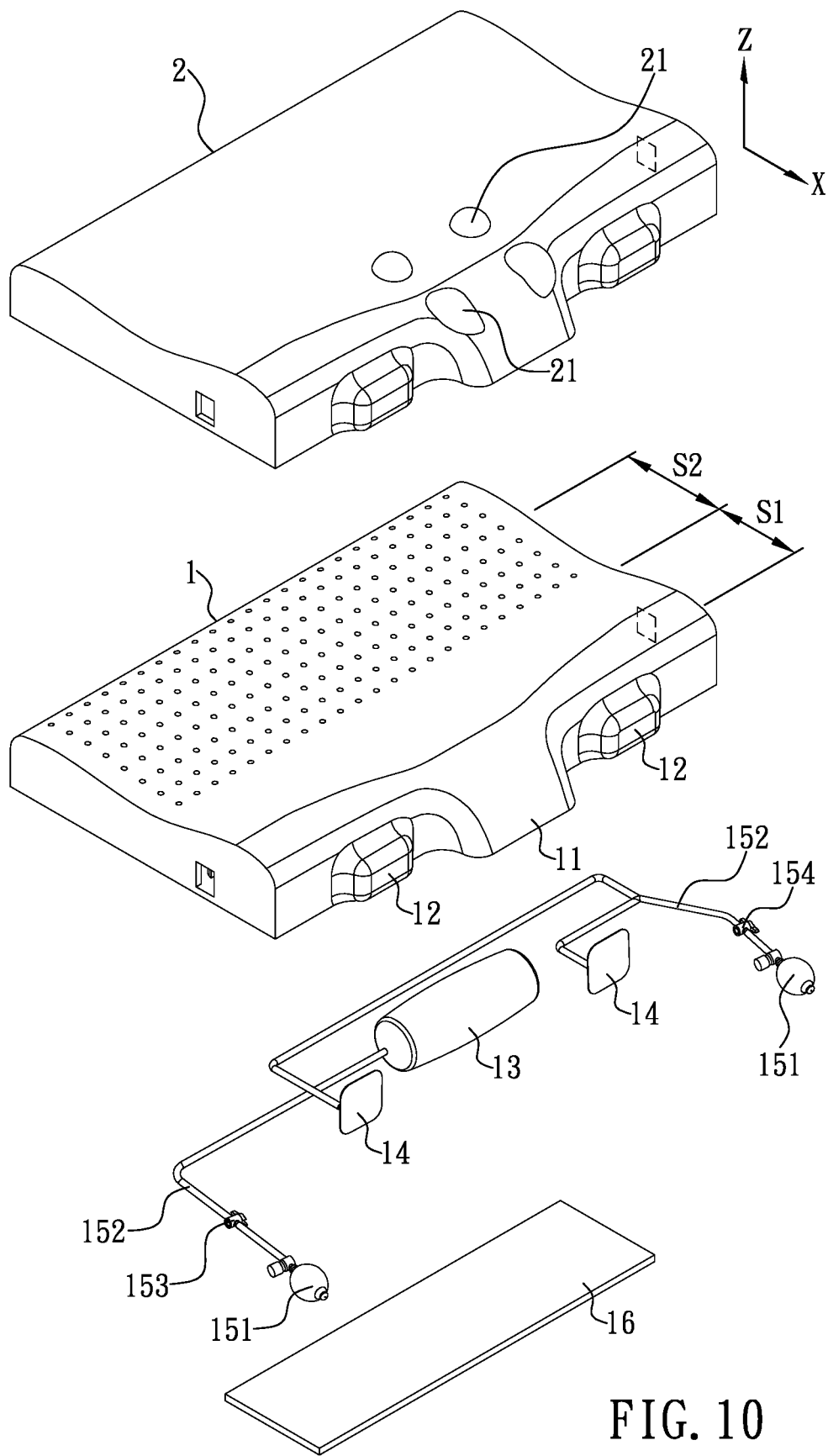
FIG. 10 is a top exploded view of the neck traction device having the plurality of inflation portions according to the present disclosure.
Figure 11:
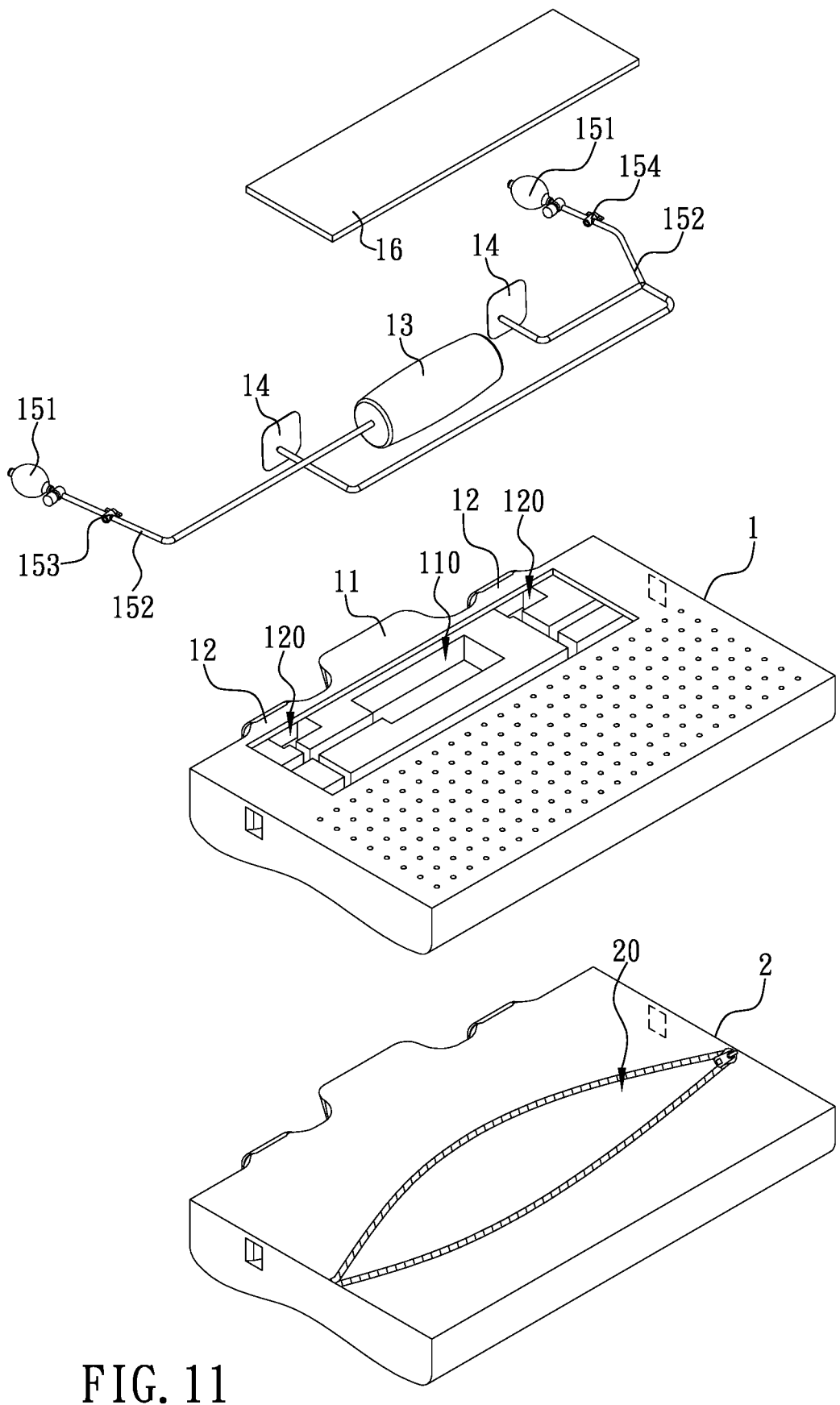
FIG. 11 is a bottom exploded view of the neck traction device having the plurality of inflation portions according to the present disclosure.

Referring to FIGS. 9-11, in certain embodiments, the inflation device 15 includes a plurality of inflation portions 151. The inflation portions 151 can be hand press inflation pumps. A first one of the inflation portions 151 can be connected to at least one of the pipe bodies 152 and communicate with the first airbag 13 through the pipe bod(ies) 152 corresponding to the inflation portion 151 that corresponds to and can communicate with the first airbag 13. The first air valve 153 can be assembled to one of the pipe bod(ies) 152 corresponding to the inflation portion 151 that corresponds to and can communicate with the first airbag 13. A second one of the inflation portions 151 can be connected to at least another one of the pipe bodies 152 and communicate with the second airbags 14 through the pipe bod(ies) 152 corresponding to the inflation portion 151 that corresponds to and can communicate with the second airbags 14. The second air valve 154 can be assembled to one of the pipe bod(ies) 152 corresponding to the inflation portion 151 that corresponds to and can communicate with the second airbags 14.

Figure 12:
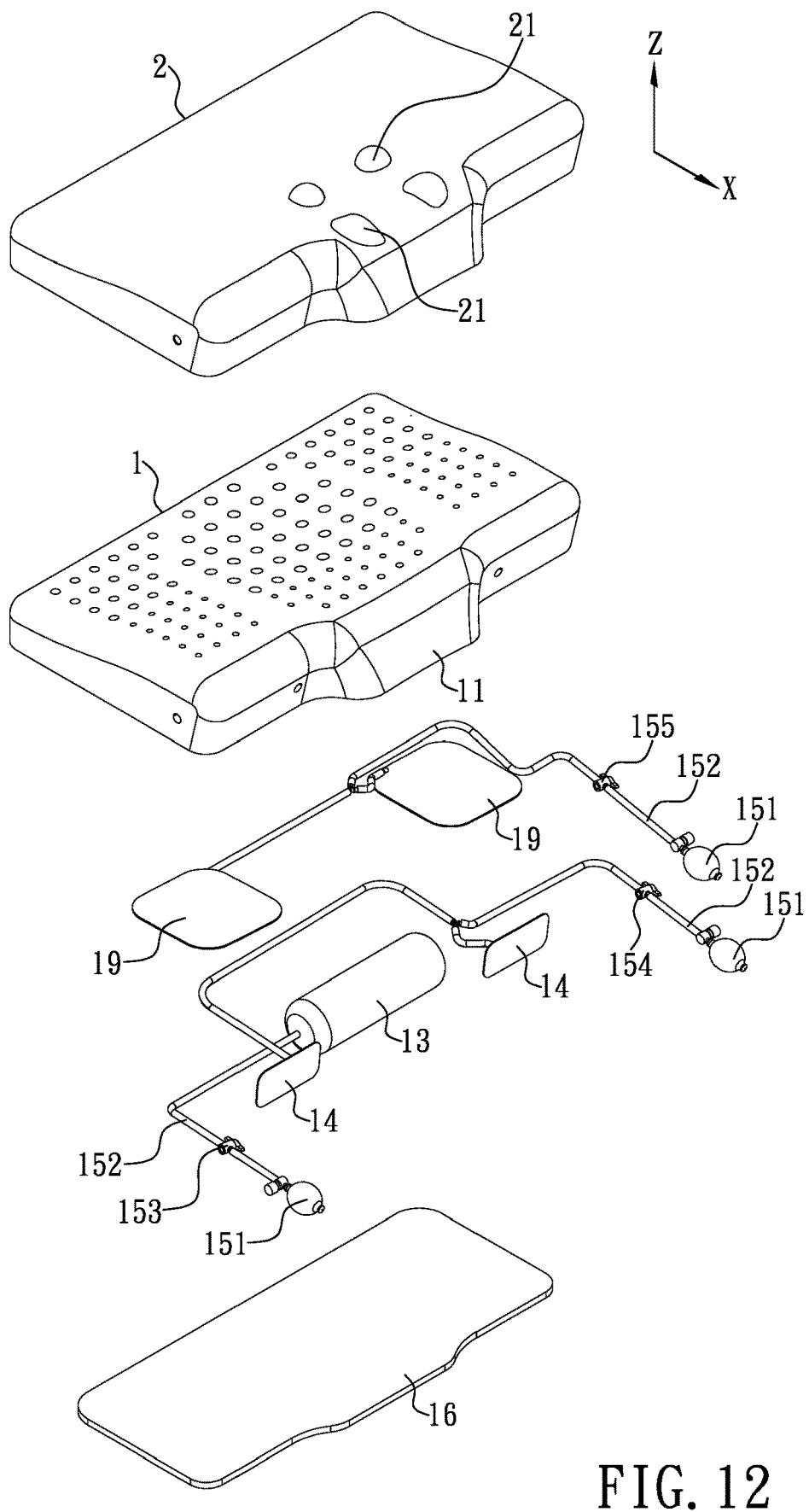
FIG. 12 is a top exploded view of the neck traction device having third airbags according to the present disclosure.
Figure 13:
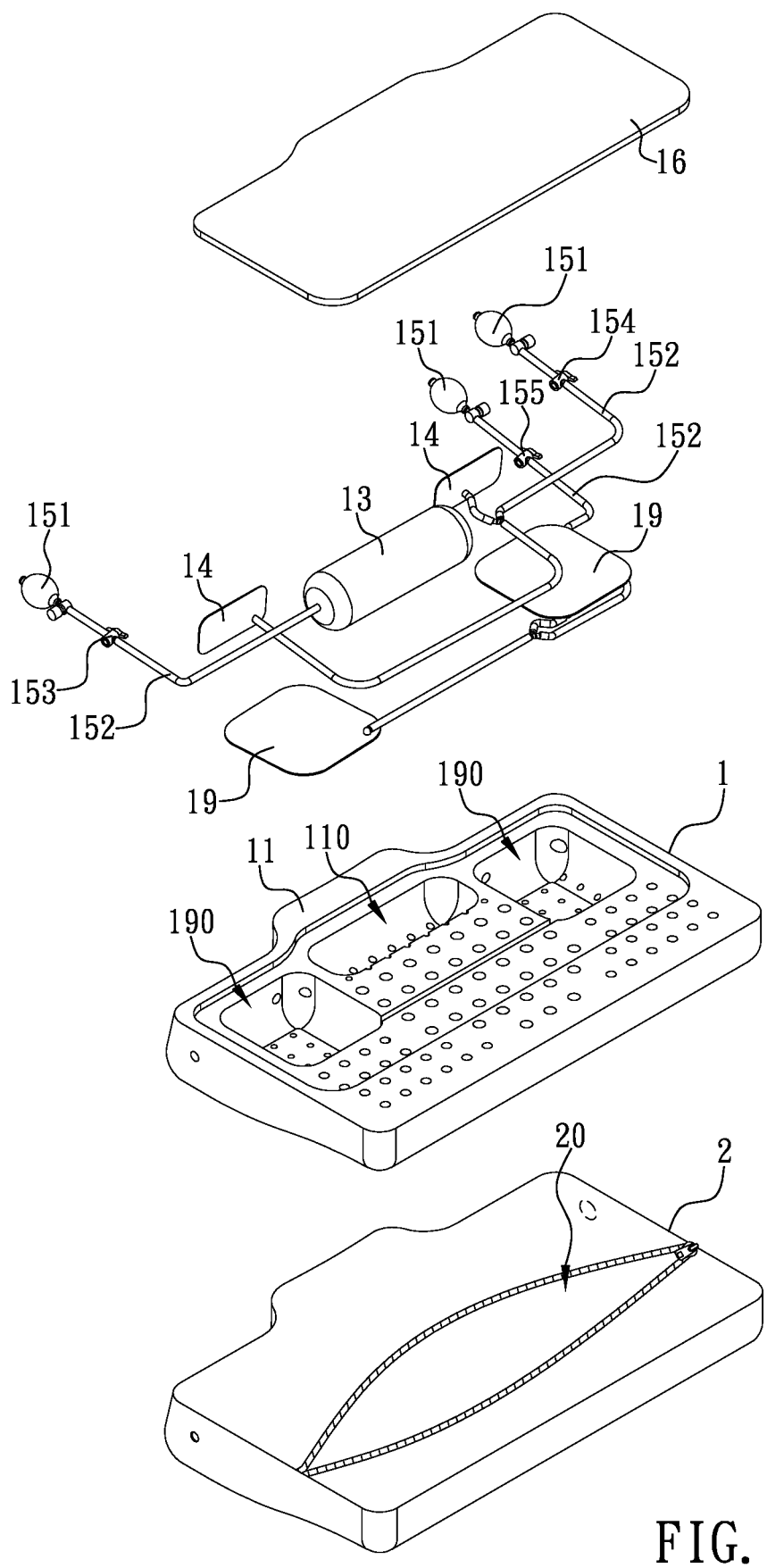
FIG. 13 is a bottom exploded view of the neck traction device having third airbags according to the present disclosure.
Figure 14:
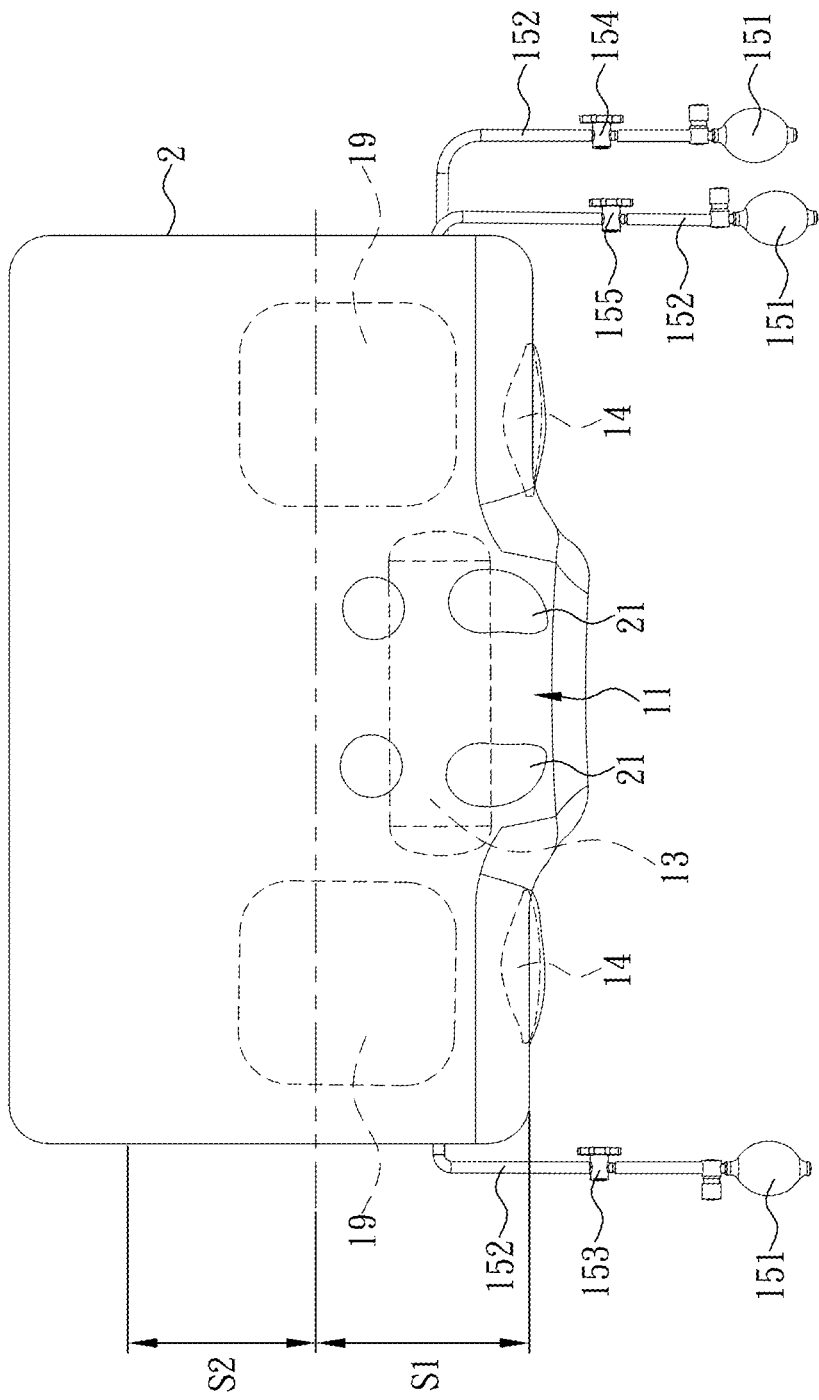
FIG. 14 is a top view of the neck traction device showing the relative positions of the first, second and third airbags according to the present disclosure.

Referring to FIGS. 12-14, in certain embodiments, the neck traction device S further includes at least two inflatable third airbags 19, in addition to the first airbag 13 and the second airbags 14. The bottom surface of the pillow body 1 can be concavely provided with two third grooves 190 at two opposite sides of the first groove 110 and adjacent to the opposite ends of the pillow body 1, respectively, for example, one adjacent to a right side of the pillow body 1, and the other one adjacent to the left side of the pillow body 1. The third airbags 19 can be accommodated in the third grooves 190, respectively, and be inflated to expand, or deflated to contract, along the first axis (for example, the Z axis shown in FIG. 12). Each of the third airbags 19 has a first portion positioned in the supporting portion S1 and a second portion positioned in the bearing portion S2, and the first portion is larger than the second portion. When the third airbags 19 expand or contract along the first axis, the expansion or contraction displaces the top surface of the pillow body 1, and therefore also the top surface of the pillowcase 2, along the first axis, for example, upward or downward, which can help to further block the head and shoulder of a user from sliding sideways and away from the neck supporting body 11 due to the movement of the first airbag 13 and/or second airbags 14 during the usage of the neck traction device S, so as to better anchor the head and neck of a user at the position on the neck traction device S that corresponds to the first airbag 13, which position is shown in FIG. 14 for reference, and with such anchoring also maintain proper positioning of the shoulders of the user relative to the positions on the neck traction device S that corresponds to the second airbags 14, which positions are also shown in FIG. 14 for reference, so that excellent traction, electrotherapy and/or heat therapy effects can be ensured.

Further, the addition and arrangement of the third airbags 19 to and for the neck traction device S can also enable a user who is used to sleep on his or her side, that is, a side sleeper, to adjust the height and firmness of the side areas of the neck traction device S on which the side sleeper rests his or her side of the head when the side sleeper is laying sideways on the neck traction device S. While a user of the neck traction device S according to the present disclosure who is accustomed to sleeping on his or her back, that is, a back sleeper, can adjust the height and firmness of the area of the neck traction device S that corresponds to the neck support body 11 and the first airbag 13 and to his or her neck when he or she is sleeping on his back, by inflating or deflating, and changing the expansion or contraction degree of, the first airbag 13, so as to better support his or her cervical spine and restore the lordotic curvature of his or her cervical spine to a natural state, the height and firmness adjustment of the neck support body 11 and the first airbag 13 may not be sufficiently satisfactory in terms of head and cervical spine support and spine alignment and maintenance for a side sleeper who is more used to lay sideways on the neck traction device S and on an area of the neck traction device S that is away from the neck support body 11 and the first airbag 13. Moreover, a side sleeper may even need extra head and neck support and spine alignment restoration and maintenance than a back sleeper does due to a greater vertical distance between the shoulder and the head/neck when he or she is in a side-sleeping posture, for example, sleeping on the side of his or her head, than between the back and the head/neck when a back sleeper is in a back-sleeping posture. Referring again to FIGS. 12-14, the neck traction device S with the third airbags 19 provides the further head and cervical spine support and spine alignment restoration and maintenance needed by a side sleeper, as the side sleeper may also adjust, in addition to the height and firmness of the area of the neck traction device S that corresponds to the neck support body 11 and the first airbag 13, the height and firmness of the side areas of the neck traction device S, for example, areas of the top surface of the pillow body 1 and of the top surface of the pillowcase 2 that are adjacent respectively to the right and left sides of the pillow body 1 and the pillowcase 2 and corresponding to, and can be displaced by the expansion or contraction of, the third airbags 19, by inflating or deflating, and changing the expansion or contraction degree of, the third airbags 19 when the side sleeper rests the side of his or her head on these side areas of the neck traction device S. That is, a side sleeper can adjust the height and firmness of the area of the neck traction device S that supports the side of the head when he or she is sleeping on his or her side, so as to arrive at a height and firmness that he or she deems proper for supporting his or her head and neck and to maintain and restore his or her spine in alignment and neutral position. Accordingly, with the features of and advantages provided by the first airbag 13, the second airbags 14 and the third airbags 19, the neck traction device S is also suitable for both back sleepers and side sleepers as an everyday sleeping pillow.

Referring again to FIGS. 12 and 13, the inflation device 15 can also be connected to the third airbags 19, so as to inflate or deflate and change the expansion or contraction degree of the third airbags 19. A third one of the inflation portions 151 can be connected to at least another one of the pipe bodies 152 and communicate with the third airbags 19 through the pipe bod(ies) 152 corresponding to the inflation portion 151 that corresponds to and can communicate with the third airbags 19. A third air valve 155 can be assembled to one of the pipe bod(ies) 152 corresponding to the inflation portion 151 that corresponds to and can communicate with the third airbags 19. When the third air valve 155 is opened, the inflation portion 151 can inflate or deflate the third airbags 19 at the same time. When the third air valve 155 is closed, the inflation portion 151 would not be able to inflate or deflate the third air bags 19. In certain embodiments, two third air valves 155 can be provided to independently adjust the degrees of inflation or deflation of any of the third airbags 19. However, the present disclosure is not limited thereto, and in certain other embodiments the inflation portions 151 corresponding to the first airbag 13, second airbags 14 and/or third airbags 19 may instead be one electric inflation pump that can control the inflation and/or deflation of the first airbag 13, second airbags 14 and/or third airbags 19 respectively or simultaneously.

Figure 15:
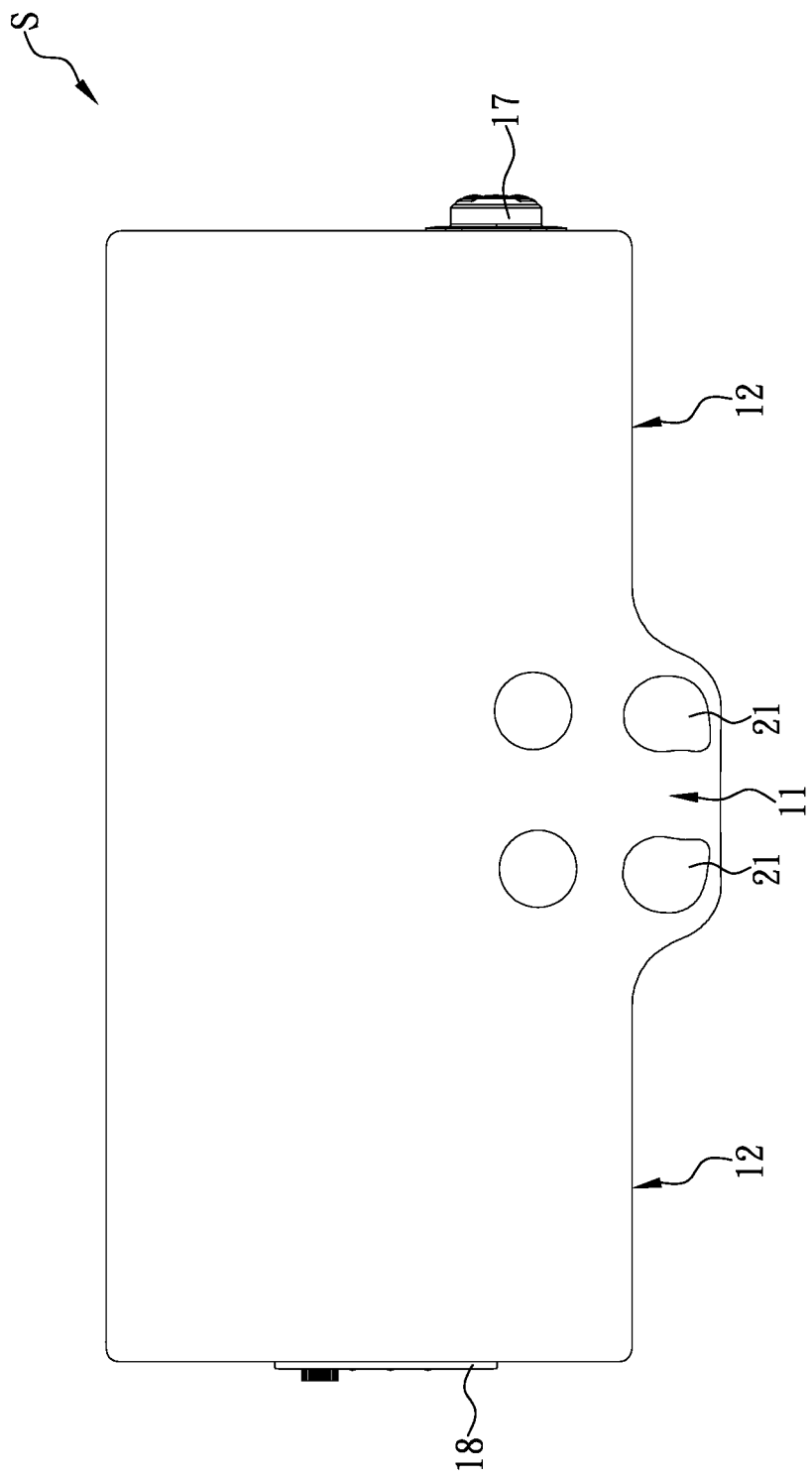
FIG. 15 is a top view of the neck traction device according to certain other embodiments of the present disclosure.
Figure 16:
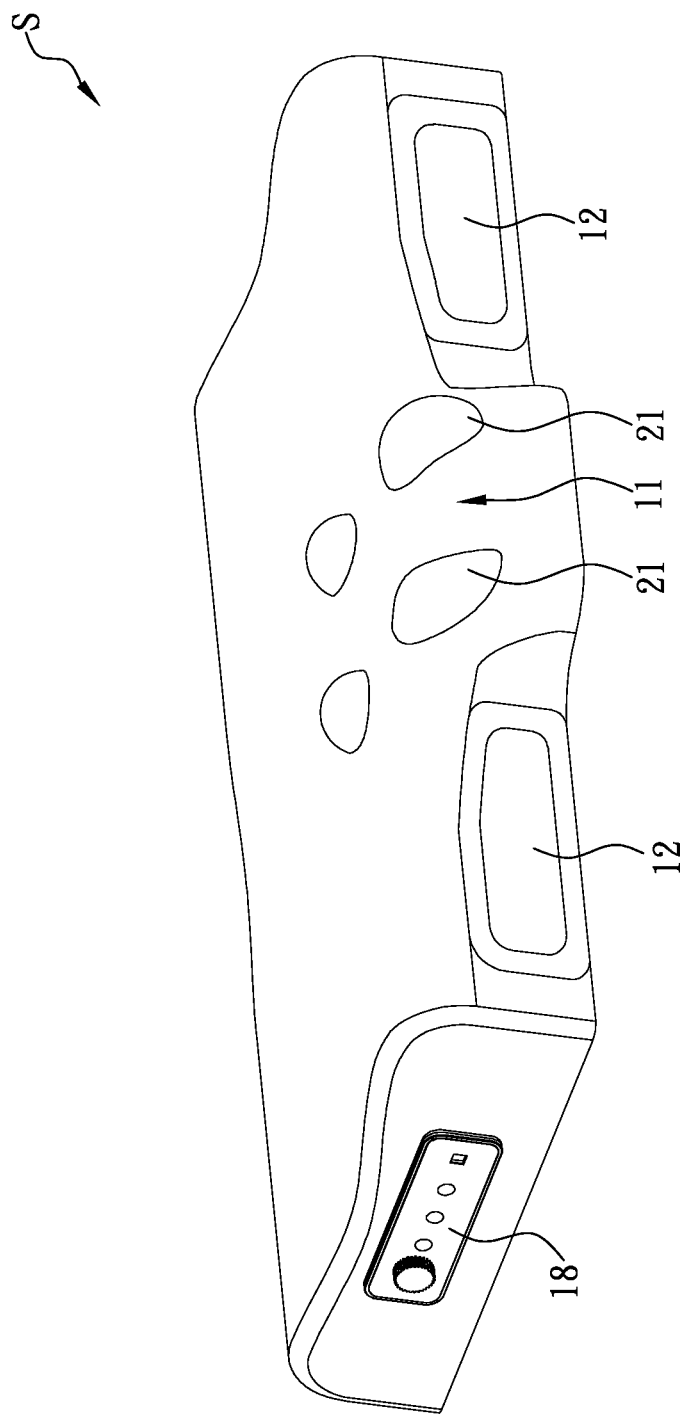
FIG. 16 is a perspective view of the neck traction device according to certain other embodiments of the present disclosure.
Figure 17:
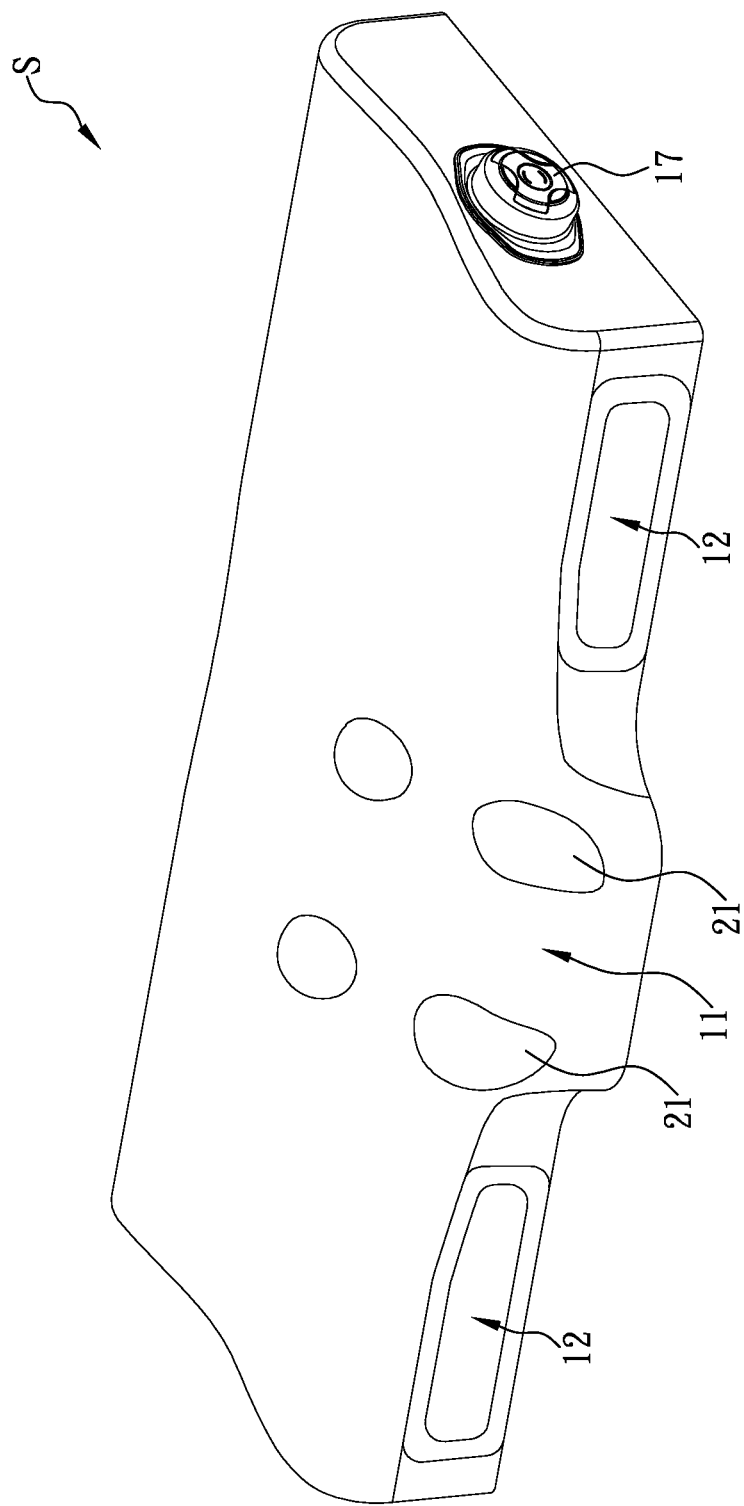
FIG. 17 is another perspective view of the neck traction device according to certain other embodiments of the present disclosure.
Figure 18:
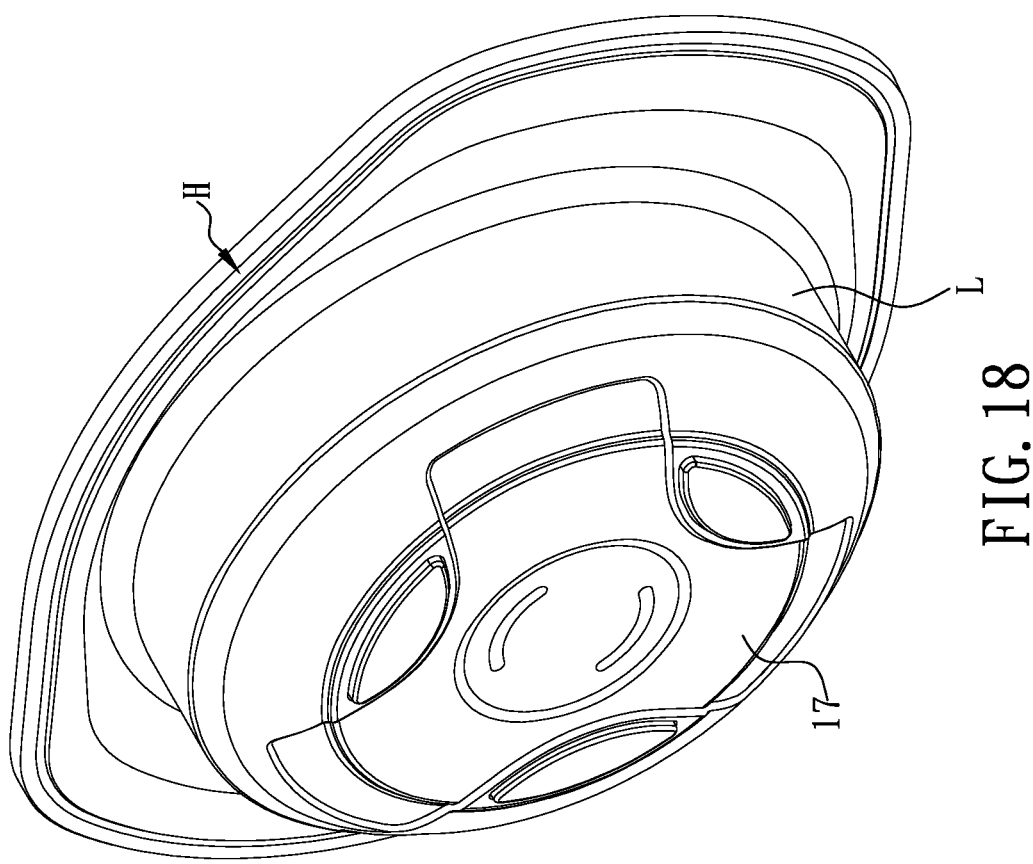
FIG. 18 is an assembled view showing a physical therapy device being harnessed in a holder by a secure releasable locking mechanism according to certain embodiments of the present disclosure.
Figure 19:
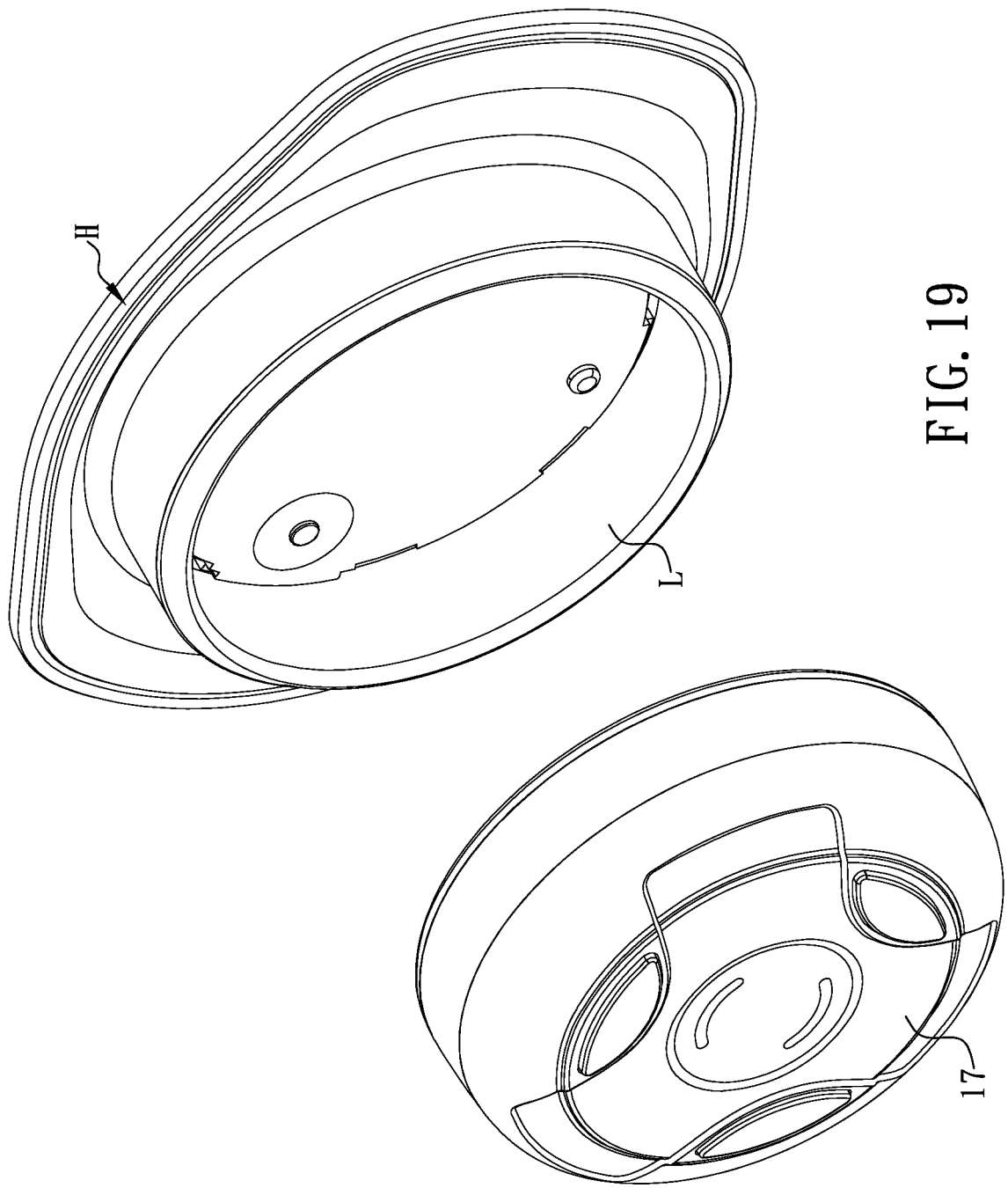
FIG. 19 is an exploded view of the assembly of the physical therapy device and the holder according to certain embodiments of the present disclosure.
Figure 20:
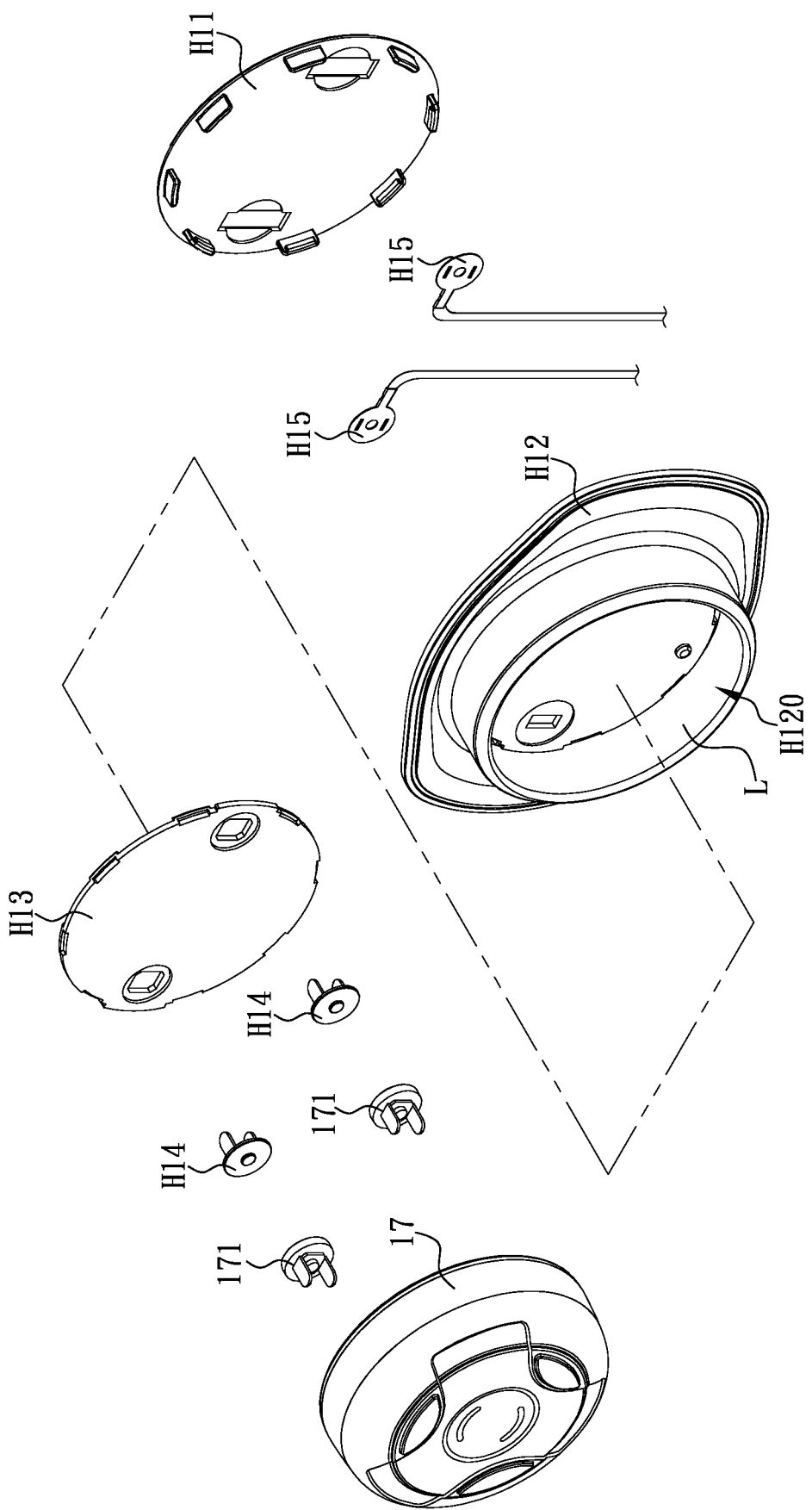
FIGS. 20 and 21 are exploded views showing the detailed components of the physical therapy device, the secure releasable locking mechanism and the holder according to certain embodiments of the present disclosure.
Figure 21:
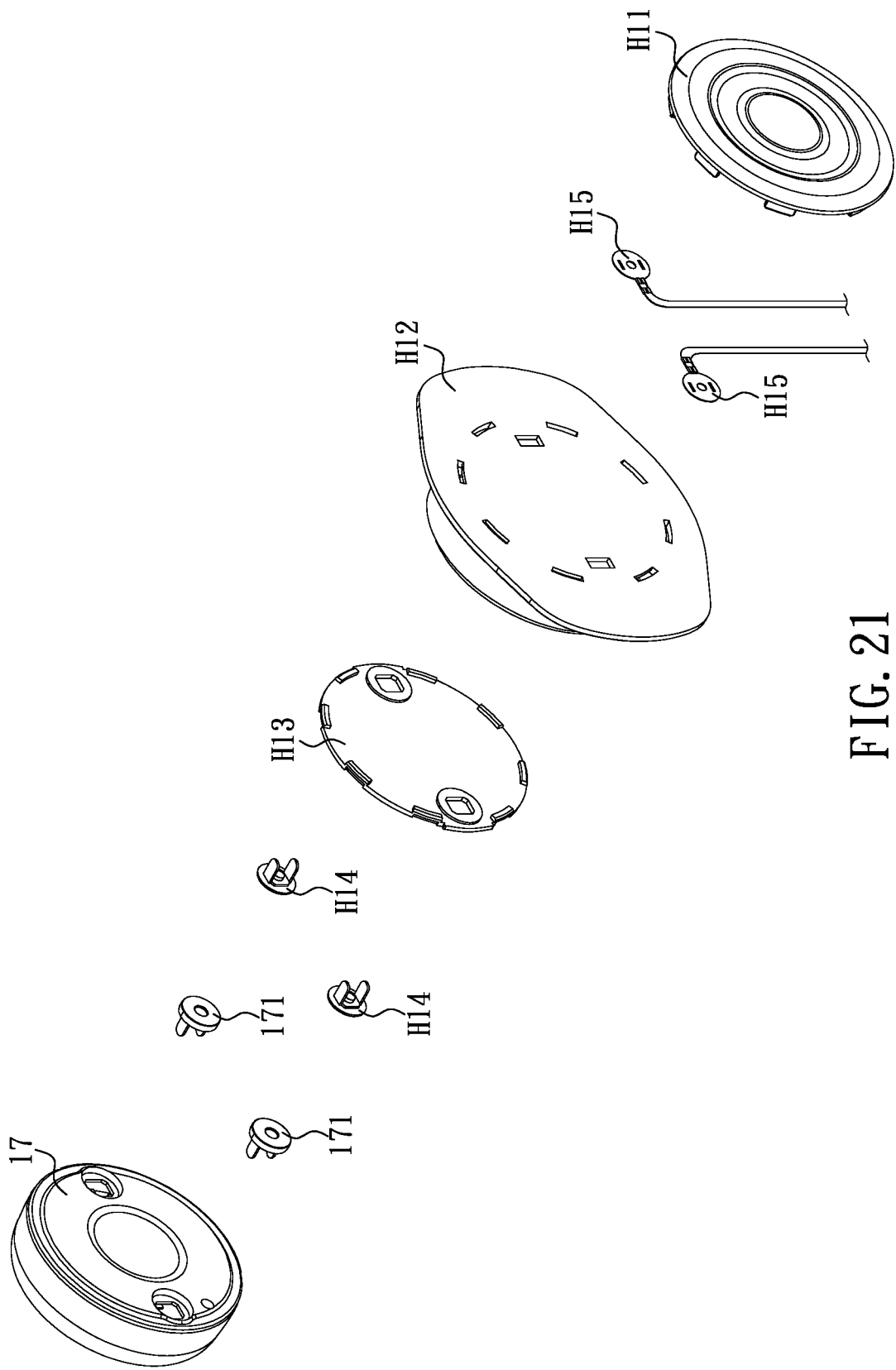

It is noted that the present disclosure is not limited to the embodiments as shown in FIG. 1 where the shoulder abutting bodies 12 extends from and are shaped as protrusions on the front surface of the supporting portion S1 when the second airbags 14 are not inflated. Referring to FIGS. 15-17, in certain embodiments, shoulder abutting bodies 12 are arranged on the two sides of the neck supporting body 11 without extending from or being shaped as protrusions on the front surface of the supporting portion S1 when the second airbags 14 are not inflated. When the second airbags 14 are inflated to expand, the two shoulder abutting bodies 12 gradually protrude outward from the supporting portion S1, and accordingly abut against and push the shoulders of the user. Referring to FIGS. 12-14, in certain embodiments, the second grooves 120 may be omitted, and the second airbags 14 may be arranged external to the pillow body 1 and at positions on the pillow body 1 that correspond in position to the shoulder abutting bodies 12, instead of being accommodated in the second grooves 120, and can displace, when inflated or deflated, the corresponding surface portions of the pillowcase 2 along the second axis to achieve traction effects.

Referring to FIG. 16, in certain embodiments, one side of the neck traction device S is arranged with an electric inflation device 18. The electric inflation device 18 includes an electric inflation pump, and has at least one pipe body, a first air valve, a second air valve and a third air valve that are embedded within and not exposed from the neck traction device S. Accordingly, a user can easily inflate or deflate the first airbag 13, the second airbags 14 and the third airbags 19 by operating at a control panel of the electric inflation device 18.

When a user uses the neck traction device S, in addition to utilizing the inflation effect of the first air bag 13 and the second air bags 14 to stretch the muscles of the neck and shoulder(s) so as to achieve the effect of cervical traction therapy, physical therapy such as electrotherapy and/or heat therapy can also at the same time be performed on the user to relax the tight muscles of the neck and shoulders, so as to improve local blood circulation and relieve pain in the head, neck and shoulders, throbbing arm pain and arm numbness.

Referring to FIGS. 1-5, the neck traction device S can also be provided with a plurality of physical therapy portions 21 that are substantially located at positions corresponding to the neck support body 11. When the user's head rests on the neck traction device S, the physical therapy portions 21 can abut against the neck of the user. The physical therapy portions 21 can be electrically connected to a physical therapy device 17, as shown in FIG. 17, to receive electric power transmitted from the physical therapy device 17, so that the physical therapy portions 21 can produce the effects of electrotherapy and/or thermotherapy. In certain embodiments, the physical therapy device 17 is a low-frequency therapy device (also referred to as transcutaneous electrical nerve stimulator, TENS) or an electrical muscle stimulation (EMS) device. At least one button may be arranged on the physical therapy device 17, so that a user can operate on the button to enable the physical therapy device 17 to start outputting and/or stop outputting electrical pulses, and/or outputting electrical pulses of different magnitudes and/or frequencies. In certain embodiments, the physical therapy device 17 is configured to receive wireless signals, such as signals using wireless network protocols or technology standards such as Bluetooth® and/or WiFi™, so that a user can operate on a wireless controller to control the physical therapy device 17 to start outputting and/or stop outputting electrical pulses, and/or outputting electrical pulses of different magnitudes and/or frequencies. In certain embodiments, at least one of the physical therapy portions 21 and the physical therapy device 17 can be arranged on the pillowcase 2, and can be removed from the pillowcase 2, so that the pillowcase 2 may be washed without damaging any of the physical therapy portions 21 and the physical therapy device 17, while in certain other embodiments, at least one of the physical therapy portions 21 and the physical therapy device 17 may be arranged on the pillow body 1, and the pillowcase 2 may be provided with a through hole through which the physical therapy device 17 can be exposed from the pillowcase 2. However, the present disclosure is not limited thereto.

Referring to FIGS. 18-27, the physical therapy device 17 can be held on the neck traction device S by a holder H that is designed with a secure releasable locking mechanism L to fix the physical therapy device 17 on, and release the physical therapy device 17 from, that is, the physical therapy device 17 can be removed from, the holder H on demand. Therefore, whenever the neck traction device S needs to be washed in water, for example, to wash the pillowcase 2, the physical therapy device 17 can be removed from the holder H to prevent damage to the physical therapy device 17. In certain embodiments, the holder H with the releasable locking mechanism L may be a harness with a releasable lock. The holder H can be provided with at least one conductive member to transmit the electricity produced by the physical therapy device 17 and/or the battery pack thereon/therein to the physical therapy portions 21, so that the physical therapy portions 21 can provide electrotherapy and/or heat therapy.

Referring to FIGS. 18-21, in certain embodiments, the holder H includes a base plate H11, a positioning body H12, an inner plate H13, a plurality of electrical conductive connectors H14, and a plurality of conductive-wire connectors H15. The base plate H11 and the positioning body H12 can be assembled with each other. A rear surface of the base plate H11 can be provided with at least one hook-and-loop fastener, so as to be attached to the neck traction device S, for example, to the pillowcase 2 or to the pillow body 1. The positioning body H12 can be made of at least one elastic material, and formed with an accommodating slot H120 on the front surface thereof. The inner plate H13 can be arranged on the bottom surface of the accommodating slot H120. The inner diameter of the accommodating slot H120 can be slightly smaller than the outer diameter of the physical therapy device 17, for example, being smaller by 0.1% to 5% of the outer diameter of the physical therapy device 17, and the slot wall of the accommodating slot H120 can form the releasable locking mechanism L by, when the physical therapy device 17 is placed within the accommodating slot H120, expanding to a small extent, due to the flexibility of the accommodating slot H120, to wrap and abut firmly against the periphery of the physical therapy device 17, so as to position the physical therapy device 17 on the positioning body H12. When the positioned physical therapy device 17 is pulled outward from the positioning body H12 with a force that is greater than a force by friction that is exerted by the slot wall of the accommodating slot H120 (that is, the releasable locking mechanism L) to the physical therapy device 17, the physical therapy device 17 can be removed from the releasable locking mechanism L.

Referring again to FIGS. 18-21, the electrical conductive connectors H14 can be placed in the accommodating slot H120, and extend through, in sequence, the inner plate H13 and the bottom surface of the accommodating slot H120 and to the base plate H11. The conductive-wire connectors H15 can be located between the positioning body H12 and the base plate H11, and electrically connected to the corresponding electrical conductive connectors H14 respectively. Each of the conductive-wire connectors H15 can be electrically connected with at least one external conductive wire. Further, the rear side of the physical therapy device 17 can be provided with a plurality of electrical conductive members 171. After the physical therapy device 17 is placed in the accommodating slot H120, each of the electrical conductive members 171 can be electrically connected with a corresponding electrical conductive connectors H14, so that the electric current (current pulse signals) outputted by the physical therapy device 17 can pass in sequence through the electrical conductive member 171 and the electrical conductive connectors H14 and be transmitted to the conductive-wire connector H15. However, in certain embodiments, the electrical conductive connector H14 and the conductive-wire connector H15 may be integrated into one piece, and the electrical conductive connector H14 can be electrically connected with an external conductive wire.

Figure 22:
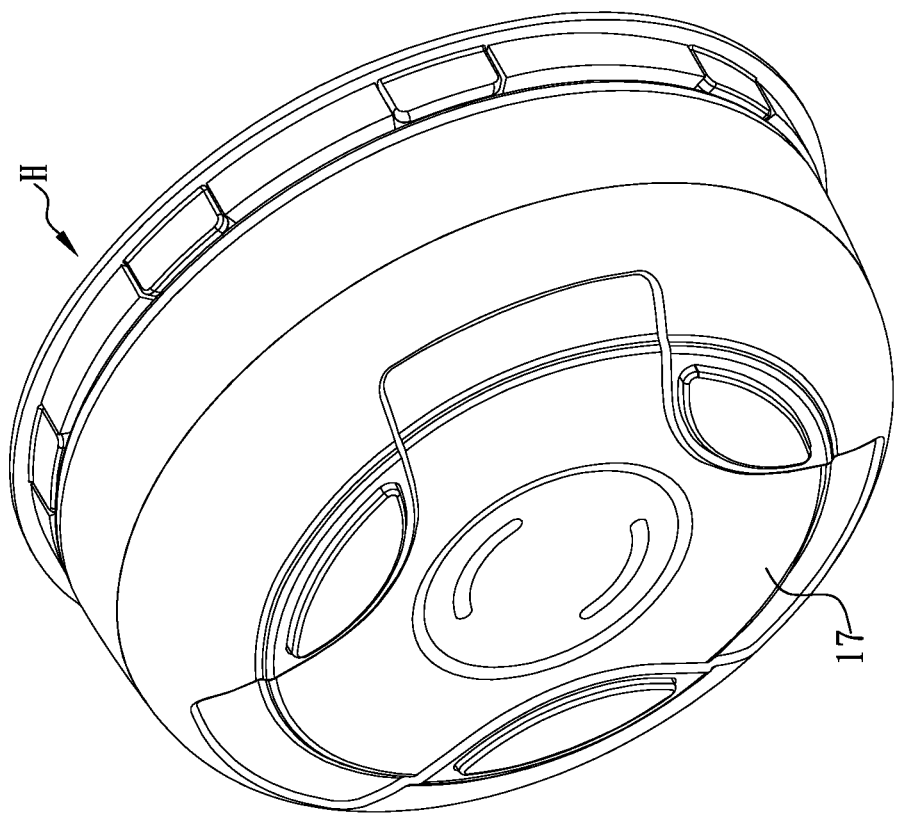
FIG. 22 is an assembled view showing the physical therapy device being harnessed in the holder according to certain other embodiments of the present disclosure.
Figure 23:
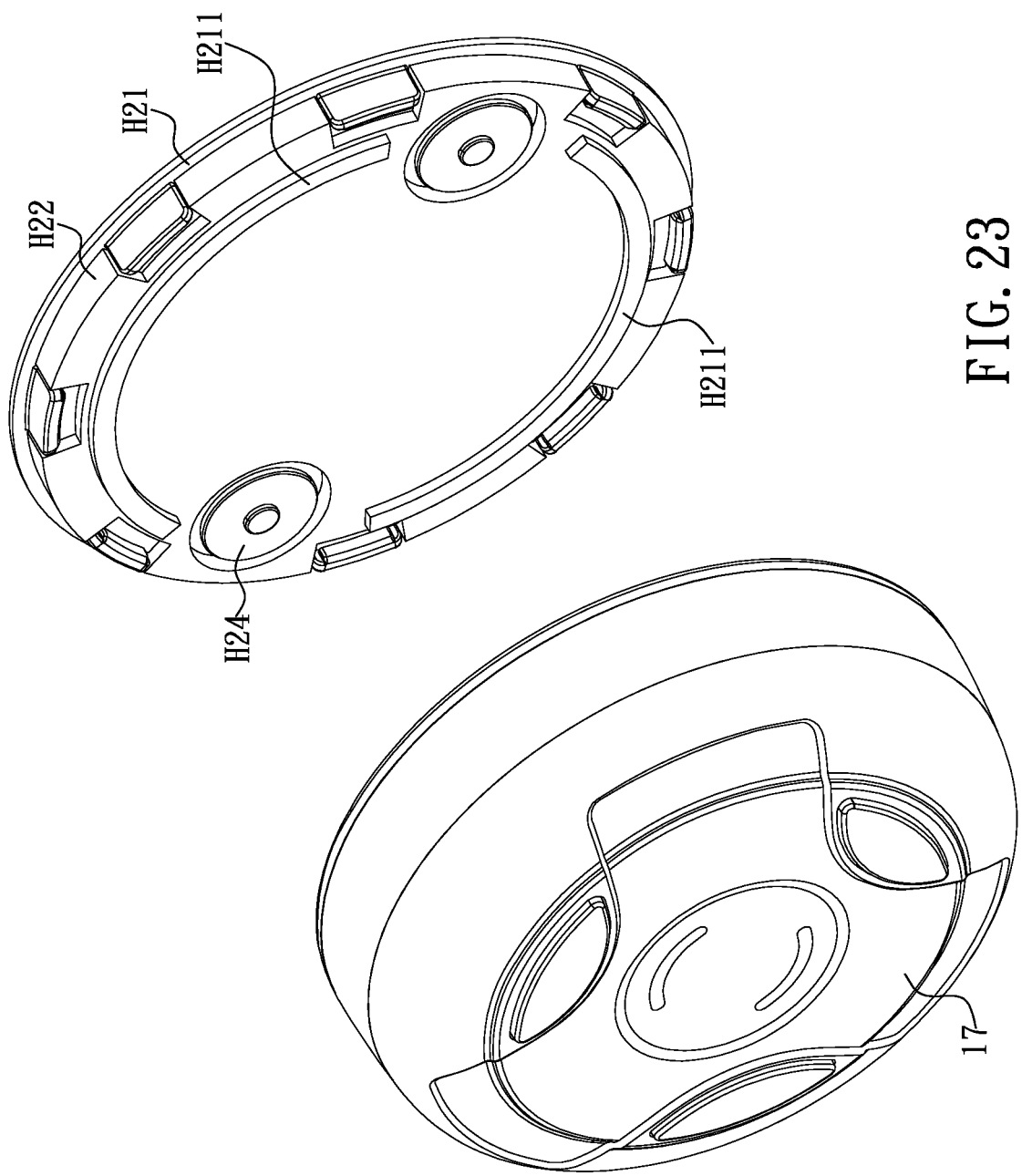
FIGS. 23 and 24 are exploded views of the assembly of the physical therapy device and the holder according to certain other embodiments of the present disclosure.
Figure 24:
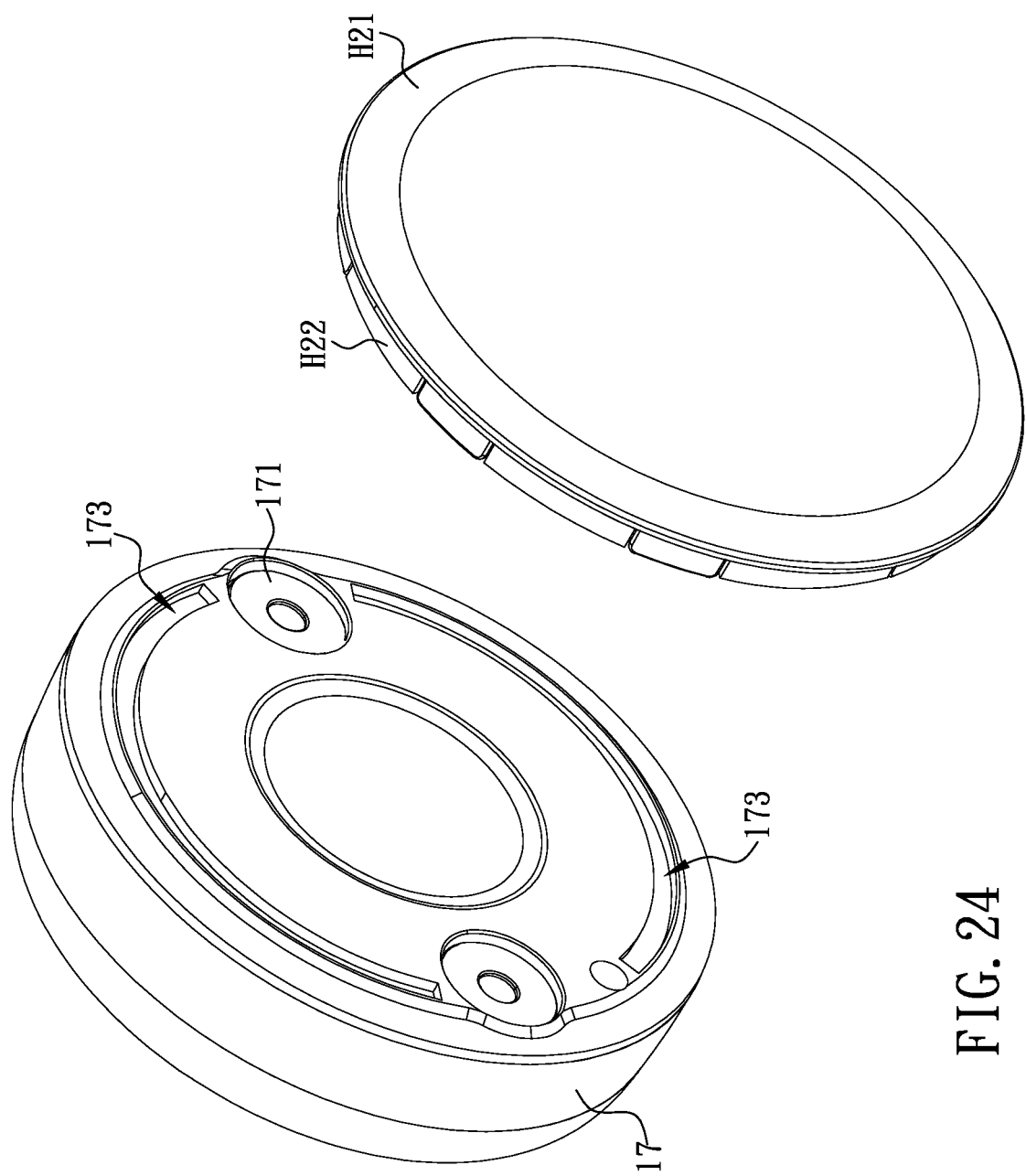

Referring to FIGS. 22-24, in certain embodiments, the holder H may include a base plate H21, a positioning body H22, and a plurality of electrical conductive connectors H24. The base plate H21 and the positioning body H22 can be assembled with each other, and the electrical conductive connectors H24 can be fixed on the positioning body H22. The front surface of the positioning body H22 can be protrudingly formed with at least one protruding rail H211 which serves as the releasable locking mechanism L. The rear surface of the physical therapy device 17 can be formed with at least one groove 173. The width and/or length of the groove 173 can be slightly smaller than the corresponding width and/or length of the protruding rail H211, for example, being smaller by 0.1% to 5% of the width of the protruding rail H211. When assembling the physical therapy device 17 to the positioning body H, the protruding rail H211 can be inserted into the corresponding groove 173, and the electrical conductive member(s) 171 can at the same time be electrically connected with the corresponding electrical conductive connector(s) H24. When the positioned physical therapy device 17 is pulled outward from the positioning body H22 with a force that is greater than the clamping force between the protruding rail(s) H211 and the corresponding groove(s) 173, the physical therapy device 17 can be removed from the releasable locking mechanism L.

Figure 25:
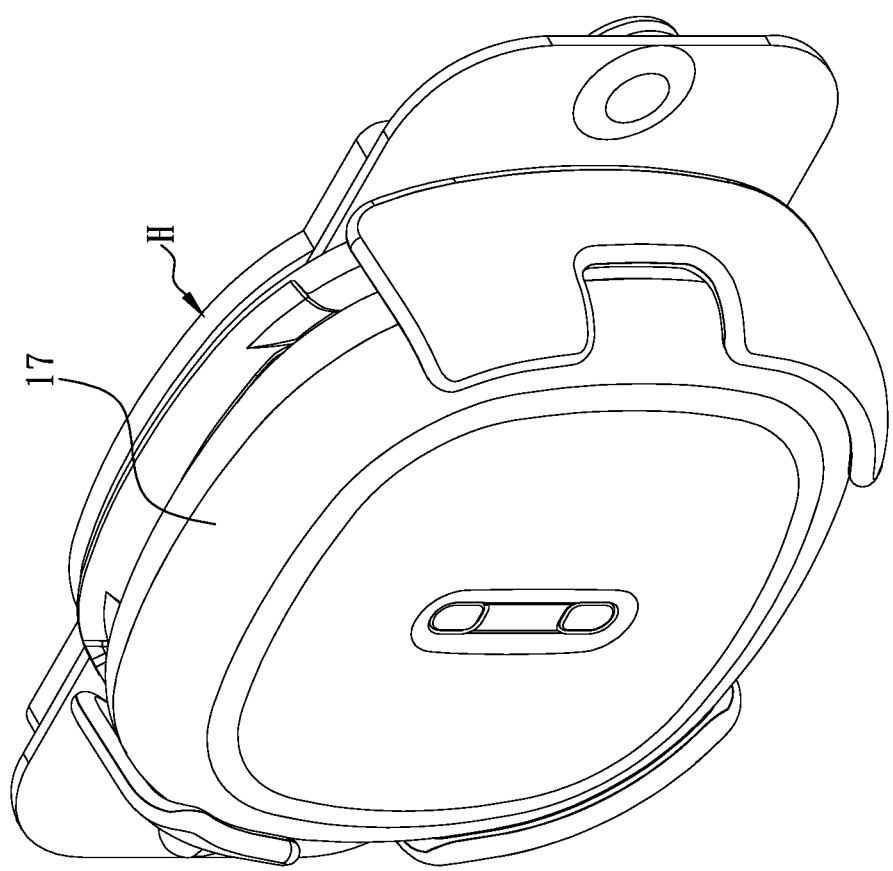
FIG. 25 is an assembled view showing the physical therapy device being harnessed in the holder according to yet certain other embodiments of the present disclosure.
Figure 26:
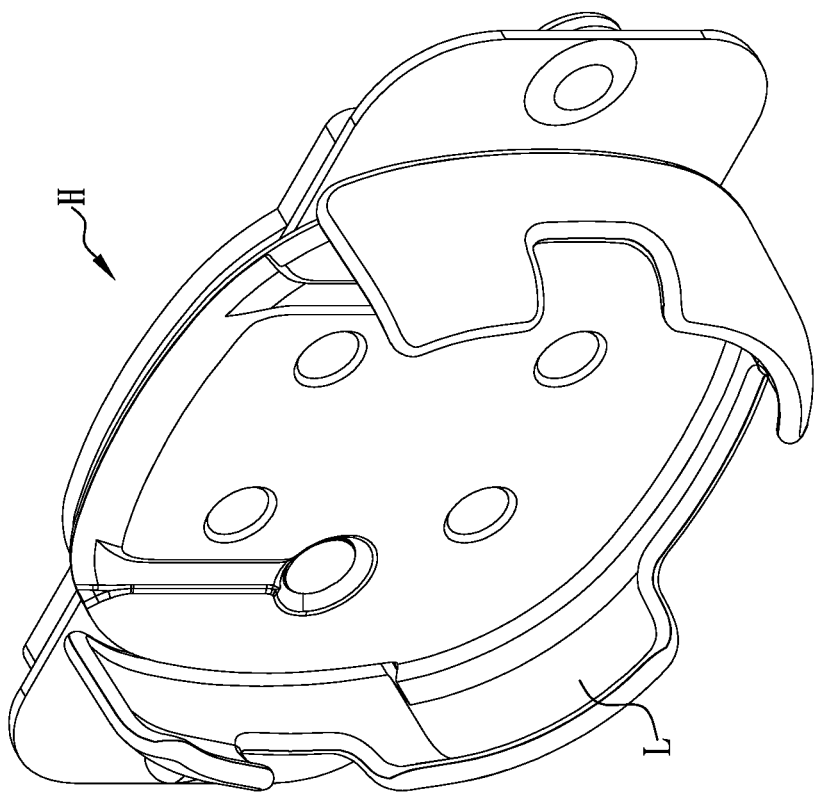
FIG. 26 is an exploded view of the assembly of the physical therapy device and the holder according to yet certain other embodiments of the present disclosure.
Figure 26:
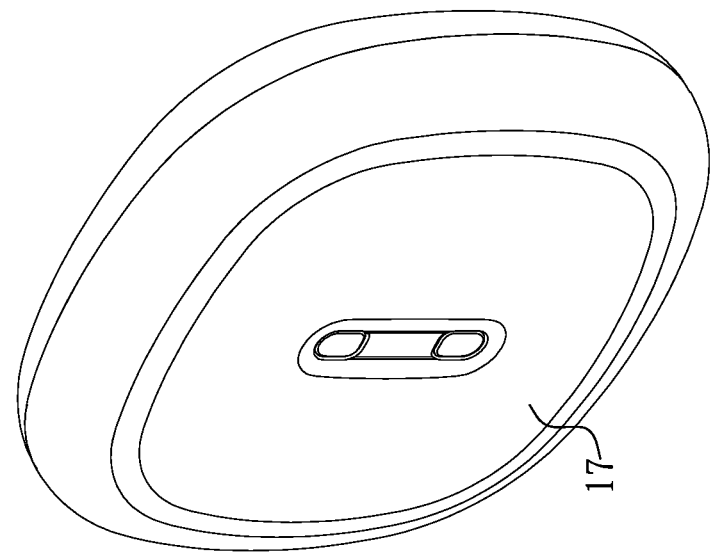
Figure 27:
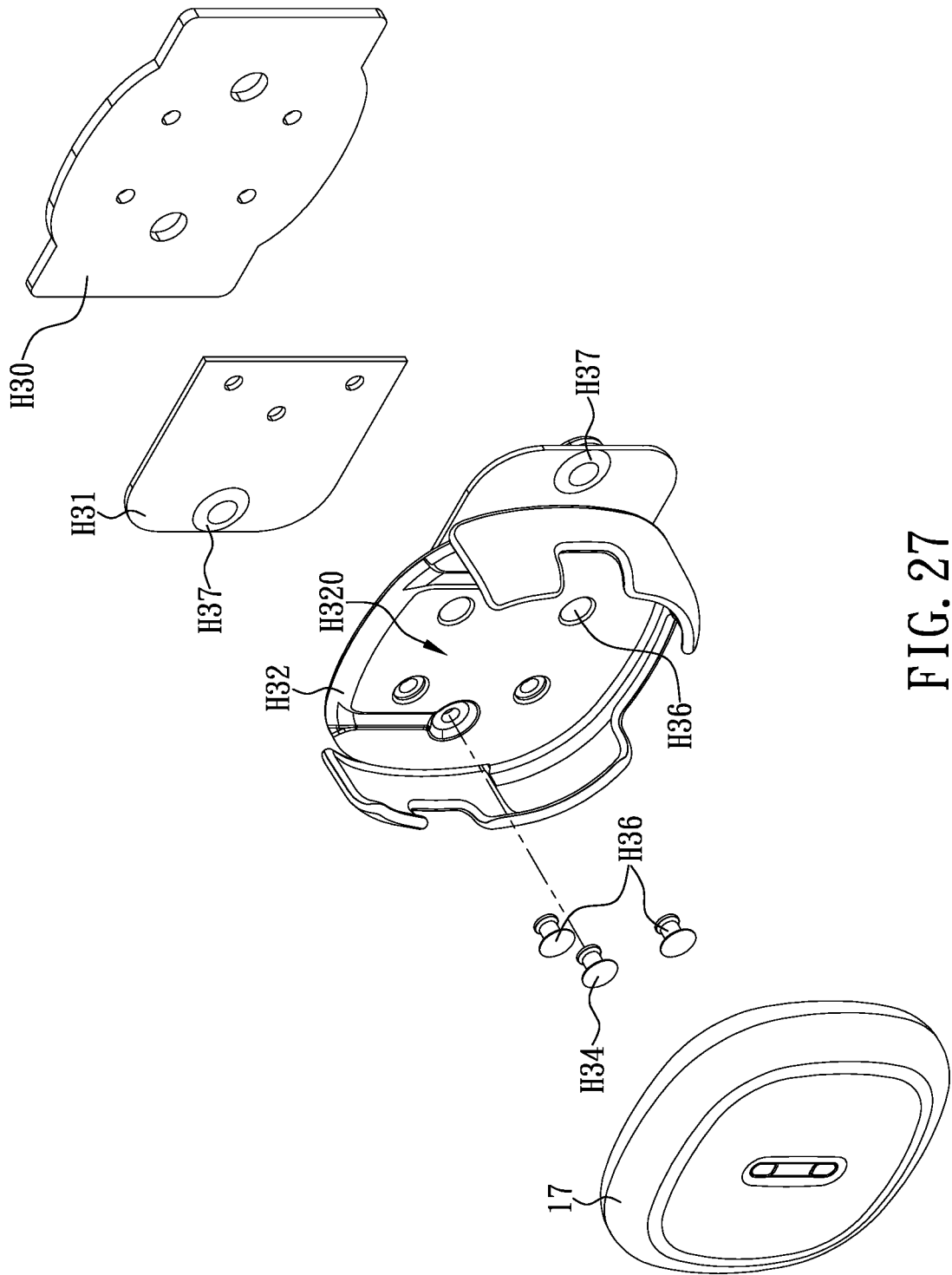
FIG. 27 is an exploded view showing the physical therapy device and the detailed components of the holder according to yet certain other embodiments of the present disclosure.

Referring to FIGS. 25-27, in certain embodiments, the holder H may include at least one base plate H31, a positioning body H32, and a plurality of electrical conductive connectors H34. The front side of the base plate H31 can abut against the rear side of the positioning body H32, and the rear side of the base plate H31 can abut against a connection plate H30 (for example, at least one hook-and-loop fastener). The base plate H31, the positioning body H32 and the connection plate H30 can be assembled into one piece through a plurality of fastening members H36. The front side of the positioning body H32 is formed with an accommodating room H320, and the physical therapy device 17 can be placed in the accommodating room H320, with the surrounding wall defining and of the accommodating room H320 forming the releasable locking mechanism L. A part of the base plate H31 that is not blocked by the positioning body H32 when the positioning body H32 and the base plate H31 are assembled can be provided with at least one fixing member H37 (for example, a button). The fixing member H37 can be buckled with a corresponding fixing member on the neck traction device S, so that the holder H can be more firmly positioned on the neck traction device S.

In other words, referring to FIGS. 18-27, the holder H may be provided with various electrical conductive/connecting members as described supra that enable electrical conduction between the physical therapy device 17 and the physical therapy portion(s) 21 and/or electrodes positioned under the neck and on the upper shoulders. Such a physical therapy device-holder-physical therapy portion set-up enables the use of TENS, EMS, and other electrotherapy/heat therapy devices to treat the neck and upper shoulders of a user, and to relieve his or her headaches, neck pain, shoulder pain and radiating pain down the arms.

Further, when the neck traction device S needs to be washed, the releasable locking mechanism L can be unlocked to release and remove the physical therapy device 17 before the neck traction device S is washed in water, so as to prevent damage to the water sensitive electronics within the physical therapy device 17. In certain embodiments, the physical therapy device 17 can be disposed directly on the neck traction device S without the holder H, and is electrically connected to the physical therapy portions 21 to transmit electricity to the physical therapy portions 21.

Figure 28A:
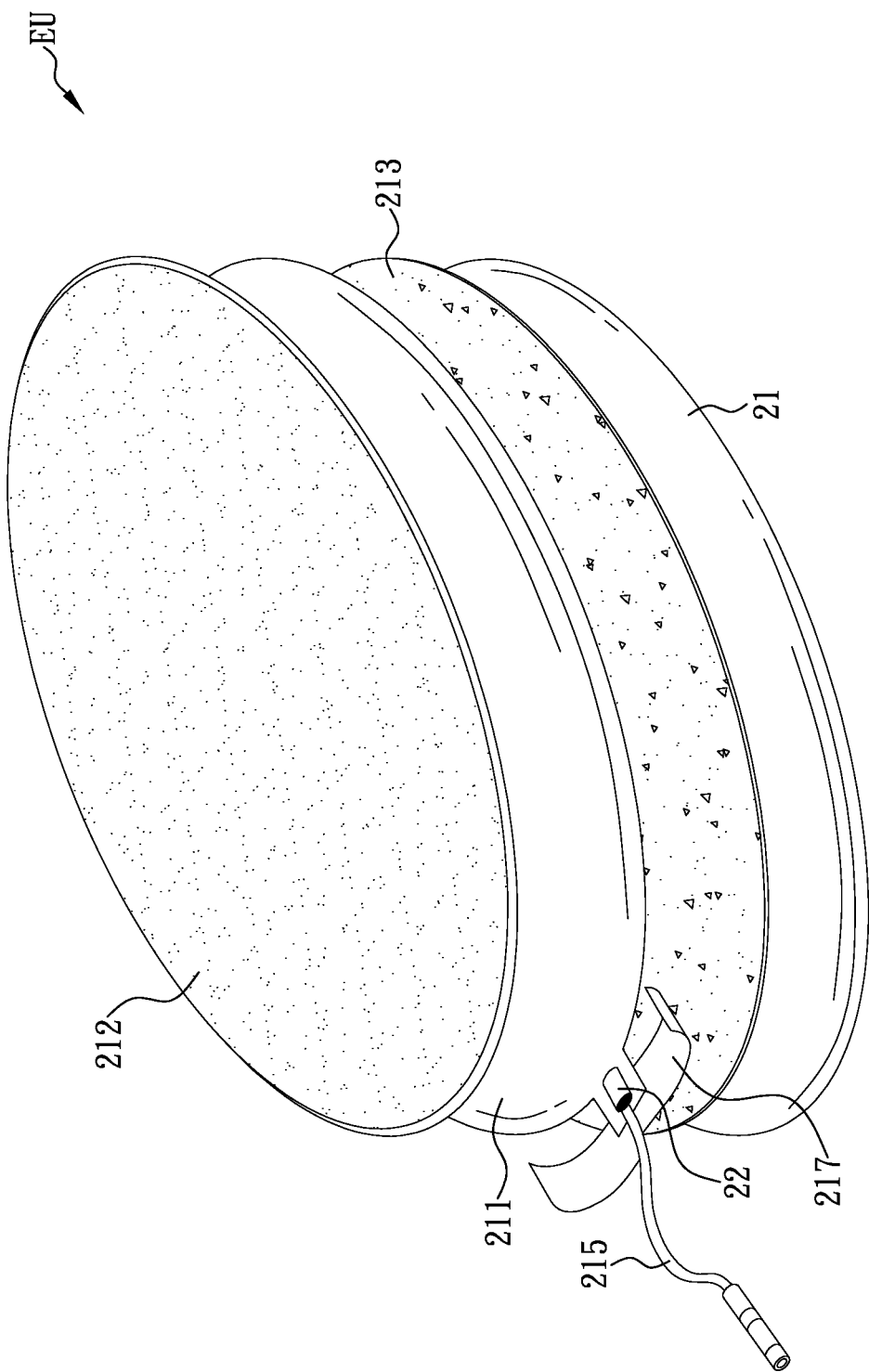
FIG. 28A is a schematic view of an electrotherapy unit arranged at a physical therapy portion according to the present disclosure.

Referring to FIG. 28A, in certain embodiments, a physical therapy portion 21 can be arranged with an electrotherapy unit EU. The electrotherapy unit EU can include a conductive layer 211, optionally a thin film layer 212, and an adhesion layer 213. The conductive layer 211 may be a layer of conductive fibers, conductive film, conductive cloth, aluminum foil, or a mixture thereof, or be made of other conductive materials. One side of the conductive layer 211 can be disposed with the optional thin film layer 212 (for example, a layer of conductive gel), while the other side of the conductive layer 211 can be disposed with the adhesion layer 213. The conductive layer 211 can be electrically connected to a metal member 22, and the metal member 22 can be electrically connected to a conductive wire 215. An insulative band 217 can be wound around and fix the metal member 22 and the conductive wire 215. The adhesion layer 213 (for example, a layer of glue) can be fixed to the pillowcase 2, or in certain embodiments, to the pillow body 1, so that for a user to use the physical therapy portion 21, as long as the conductive layer 211, or if the thin film layer 212 exists, the thin film layer 212, is abutted against his or her skin, and the conductive wire 215 is electrically connected to the physical therapy device 17, electric power from the physical therapy device 17 such as a TENS or EMS device can be received by the physical therapy portion 21, and the physical therapy portion 21 can output electrical stimulation to the neck of a user to achieve the effect of electrotherapy. However, the present disclosure is not limited thereto. In certain embodiments, when the thin film layer 212 is omitted, the conductive layer 211 is in direct contact with the skin. The adhesion layer 213 may include fabric such as nonwoven or cotton fabric, and can be connected with a conductive sheet such as an aluminum foil, so as to be better connected to the pillow body 1 or the pillowcase 2.

Figure 28B:
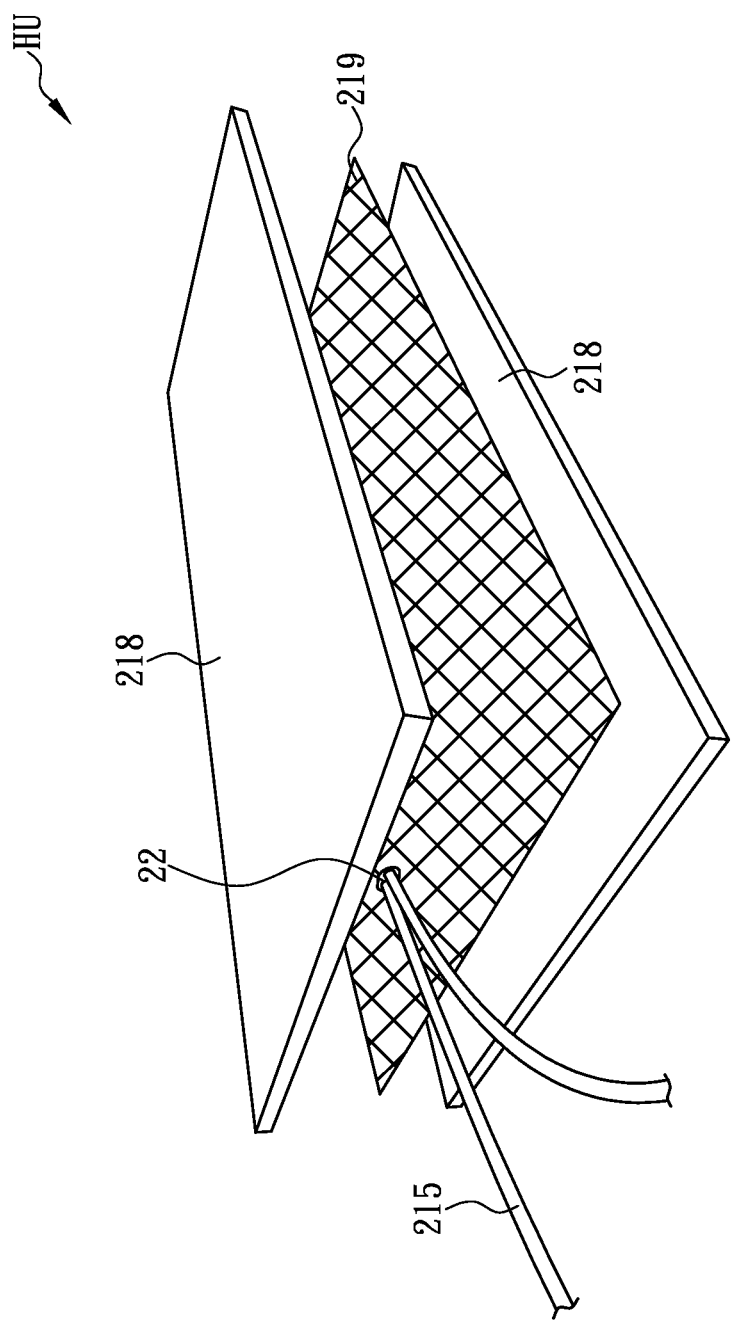
FIG. 28B is a schematic view of a heat therapy unit arranged at a physical therapy portion according to the present disclosure.

Referring to FIG. 28B, in certain embodiments, a physical therapy portion 21 can be arranged with a heat therapy unit HU. The heat therapy unit HU can include two cushion layers 218 (for example, being made of non-woven fabric) and a heat-generating layer 219. The heat-generating layer 219 can be made of metal material (e.g., iron-chromium-aluminum alloy wires, nickel-chromium alloy wires, etc.), graphene, carbon fiber material, or other electrothermal materials, etc., so as to generate heat when electric current passes therethrough. The heat-generating layer 219 can be sandwiched between the two cushion layers 218, and the outer surface of one of the cushion layers 218 can be fixated on the corresponding pillowcase 2, or in certain embodiments, to the pillow body 1. The heat-generating layer 219 can be electrically connected with the metal member 22 to receive electric power from the physical therapy device 17 through the conductive wire 215, so that the physical therapy portion 21 generates heat that is conducted away through the cushion layers 218, and heats the neck of the user to relax blood vessels and increase local blood circulation and the rate of metabolism, such that inflammatory substances are quickly expelled from the human body and self-healing abilities of the muscle tissue can be improved. At the same time, warm compresses can increase soft tissue resilience and reduce muscle spasms, so as to relieve one's pain and relax one's emotions. In certain embodiments, the cushion layers 218 may be omitted, and the heat-generating layer 219 is in direct contact with the skin.

Figure 28C:
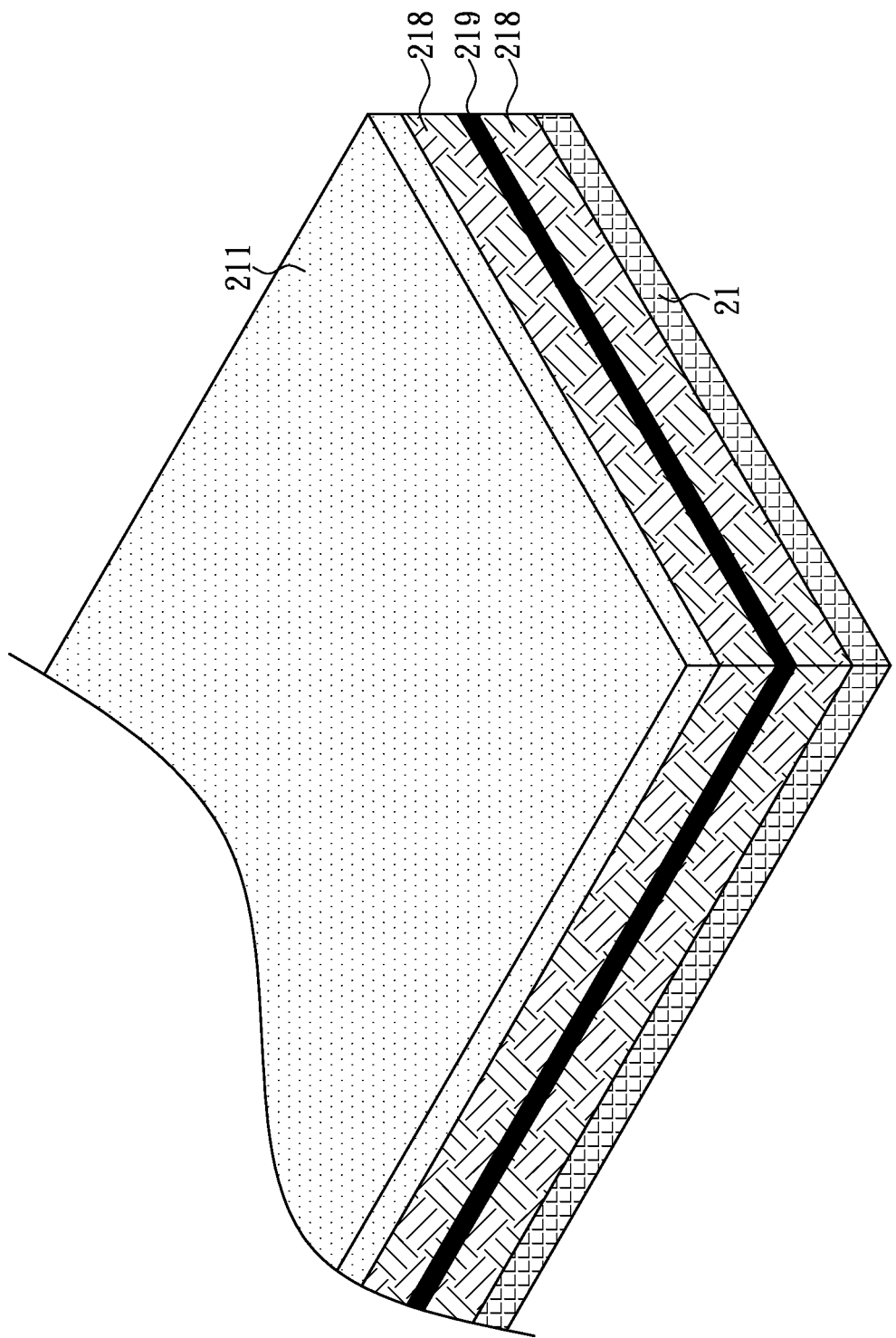
FIG. 28C is a schematic view of a combined electrotherapy-heat therapy unit arranged at a physical therapy portion according to the present disclosure.

Referring to FIG. 28C, in certain embodiments, a physical therapy portion 21 can be arranged with a combined electrotherapy-heat therapy unit. The combined electrotherapy-heat therapy unit can be formed by stacking the foregoing electrotherapy unit EU and heat therapy unit HU. For example, a heat-generating layer 219 is provided between two cushion layers 218, and the outer surface of one of the cushion layers 218 can be covered with the conductive layer 211, such as a layer of conductive fiber. The heat-generating layer 219 and the conductive layer 211 can receive electric power from the physical therapy device 17 through the same or different metal members 22. The conductive layer 211 can output electrical stimulation to the neck of the user, while the heat-generating layer 219 can generate heat which passes through the cushion layers 218 and the conductive layer 211 to heat the neck of the user.

However, the present disclosure is not limited thereto. As long as the structure of a physical therapy portion 21 can achieve the result and effects of physical therapy, such a structure is within the definition of the physical therapy portion 21 according to the present disclosure.

Referring to FIGS. 4 and 13, a bottom plate 16 can be assembled to the bottom surface of the pillow body 1 to cover the first groove 110, the third groove 190, and/or the second grooves 120, and to prevent the first air bag 13, the second air bags 14, the third air bags 19 and the pipe bodies 152 from being separated from the pillow body 1. However, in other embodiments, the bottom plate 16 may be omitted, and the first airbag 13, the second airbags 14, the third airbags 19 and the pipe bodies 152 may be held by the elasticity of the pillow body 1 or be clamped and fixed by other clamping mechanism.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching. The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A neck traction device, comprising:
a supporting portion comprising:
  a neck support body located at a center portion of the supporting portion and having a top surface configured to support a neck of a user and a bottom surface concavely provided with a first groove;
  two shoulder abutting bodies respectively extending from a front side of the supporting portion, having front surfaces configured to abut against shoulders of the user, wherein each of the shoulder abutting bodies is located at a position of the supporting portion that corresponds to a respective shoulder of the user, and a bottom surface of each of the shoulder abutting bodies is concavely provided with a second groove;
  a first airbag configured to be accommodated within the first groove, expand or contract along a first axis, and displace a top surface of the neck support body along the first axis;
  two second airbags, each configured to be accommodated within a corresponding one of the second grooves, expand or contract along a second axis perpendicular or substantially perpendicular to the first axis, and displace a front surface of a corresponding one of the shoulder abutting bodies along the second axis; and
  an inflation device configured to be connected to the first airbag and the second airbags, respectively, and inflate or deflate the first airbag and the second airbags to change expansion or contraction degrees of the first airbag and the second airbags;
  and a bearing portion configured to bear an occiput of the user when the user is in a supine position, wherein a height of a top surface of the bearing portion is lower than a height of a top surface of the supporting portion,
  wherein the neck traction device is further concavely provided with two third grooves located at opposite sides of the first groove, and further comprises two third airbags, each configured to be accommodated within a corresponding one of the third grooves with a first portion of the each of the third airbags being positioned in the supporting portion and a second portion of the each of the third airbags being positioned in the bearing portion, and the first portion being larger than the second portion so that a larger expansion of the third airbag is in the supporting portion than in the bearing portion; and
  wherein the top surface of the neck support body has a first point corresponding to a highest point of the first airbag along the first axis, a center of the front surface of the shoulder abutting body is defined as a second point, the first and second axes define a plane, a distance between a projection of the first point and a projection of the second point on the plane when the top surface of the neck support body is not displaced by expansion of the first airbag and the front surface of the shoulder abutting body is not displaced by expansion of the second airbag is defined as a first distance, a distance between a projection of the first point and a projection of the second point on the plane when the first airbag is in a first maximum expansion state and the second airbag is in a second maximum expansion state, wherein the center of the front surface of the shoulder abutting body is displaced by the second maximum expansion state of the second airbag is defined as a second distance, and a ratio of the first distance to the second distance is between 1:1.55 and 1:1.75 as a result of both displacement of the top surface of the neck support body along the first axis and displacement of the front surface of the shoulder abutting body along the second axis.

2. The neck traction device according to claim 1, wherein each of the two third airbags is configured to expand or contract along the first axis, and displace a top surface of the neck traction device along the first axis.

3. The neck traction device according to claim 1, wherein the inflation device comprises: a plurality of pipe bodies;
  a first air valve configured to be assembled to a first one of the pipe bodies;
  at least one second air valve configured to be assembled to a second one of the pipe bodies;
  and at least one inflation portion configured to be connected to the first airbag and the second airbags through the plurality of pipe bodies, inflate or deflate the first airbag when the first air valve is opened, and inflate or deflate the second airbags when the second air valve is opened.

4. The neck traction device according to claim 1, wherein the first airbag is configured to expand to the first maximum expansion state with a maximum length of the first airbag in a direction of the first axis being 75 mm to 85 mm.

5. The neck traction device according to claim 1, wherein each of the second airbags is configured to expand to the second maximum expansion state with a maximum length of the second airbag in a direction of the second axis being 55 mm to 65 mm.

6. The neck traction device according to claim 1, further comprising a plurality of physical therapy portions, each corresponding to a position of the neck support body and configured to abut against the neck of the user and be electrically connected to a physical therapy device to receive electric power transmitted from the physical therapy device.

7. The neck traction device according to claim 6, wherein at least one of the physical therapy portions is arranged with an electrotherapy unit configured to receive the electric power transmitted from the physical therapy device and output electrical stimulation to the neck of the user.

8. The neck traction device according to claim 6, wherein at least one of the physical therapy portions is arranged with a heat therapy unit configured to receive the electric power transmitted from the physical therapy device and generate heat to heat the neck of the user.

9. The neck traction device according to claim 6, wherein at least one of the physical therapy portions is arranged with a combined electrotherapy-heat therapy unit configured to receive the electric power transmitted from the physical therapy device, output electrical stimulation to the neck of the user and generate heat to heat the neck.

10. The neck traction device according to claim 6, comprising a pillow body and a pillowcase configured to cover the pillow body, wherein the neck support body and the shoulder abutting bodies are arranged on the pillow body, the first airbag and the second airbags are arranged within the pillow body, the physical therapy portions are provided on the pillowcase, the inflation device is external to the pillow body and the pillowcase, and a plurality of pipe bodies are configured to extend into the pillow body through the pillowcase.

11. The neck traction device according to claim 7, comprising a pillow body and a pillowcase configured to cover the pillow body, wherein the neck support body and the shoulder abutting bodies are arranged on the pillow body, the first airbag and the second airbags are arranged within the pillow body, the physical therapy portions are provided on the pillowcase, the inflation device is external to the pillow body and the pillowcase, and a plurality of pipe bodies are configured to extend into the pillow body through the pillowcase.

12. The neck traction device according to claim 8, comprising a pillow body and a pillowcase configured to cover the pillow body, wherein the neck support body and the shoulder abutting bodies are arranged on the pillow body, the first airbag and the second airbags are arranged within the pillow body, the physical therapy portions are provided on the pillowcase, the inflation device is external to the pillow body and the pillowcase, and a plurality of pipe bodies are configured to extend into the pillow body through the pillowcase.

13. The neck traction device according to claim 9, comprising a pillow body and a pillowcase configured to cover the pillow body, wherein the neck support body and the shoulder abutting bodies are arranged on the pillow body, the first airbag and the second airbags are arranged within the pillow body, the physical therapy portions are provided on the pillowcase, the inflation device is external to the pillow body and the pillowcase, and a plurality of pipe bodies are configured to extend into the pillow body through the pillowcase.

* * * * *